US009527969B2

(12) United States Patent
Nakamura et al.

(10) Patent No.: US 9,527,969 B2
(45) Date of Patent: Dec. 27, 2016

(54) NON-SPHERICAL RESIN PARTICLES, MANUFACTURING METHOD THEREOF, AND USE THEREOF

(75) Inventors: Masaaki Nakamura, Koka (JP); Ryosuke Harada, Koka (JP)

(73) Assignee: Sekisui Plastics Co., Ltd., Osaka-shi (JP)

( * ) Notice: Subject to any disclaimer, the term of this patent is extended or adjusted under 35 U.S.C. 154(b) by 226 days.

(21) Appl. No.: 14/129,348

(22) PCT Filed: Jun. 29, 2012

(86) PCT No.: PCT/JP2012/066761
§ 371 (c)(1),
(2), (4) Date: Dec. 26, 2013

(87) PCT Pub. No.: WO2013/002386
PCT Pub. Date: Jan. 3, 2013

(65) Prior Publication Data
US 2014/0138592 A1 May 22, 2014

(30) Foreign Application Priority Data

Jun. 30, 2011 (JP) .................................. 2011-146528
Mar. 27, 2012 (JP) .................................. 2012-072183

(51) Int. Cl.
*C08J 5/00* (2006.01)
*C08L 47/00* (2006.01)
(Continued)

(52) U.S. Cl.
CPC .. *C08J 5/00* (2013.01); *C08F 2/38* (2013.01); *C08F 220/18* (2013.01);
(Continued)

(58) Field of Classification Search
CPC ............ C08J 5/00; C08L 47/00; A61K 8/0245
(Continued)

(56) References Cited

U.S. PATENT DOCUMENTS

2006/0165989 A1* 7/2006 Takikawa .................. B01J 2/06
428/402.2
2011/0287076 A1* 11/2011 Harada ............... C09D 151/003
424/401

FOREIGN PATENT DOCUMENTS

JP 08-120005 A 5/1996
JP 2007-105873 A 4/2007
(Continued)

OTHER PUBLICATIONS

International Search Report dated Oct. 9, 2012, issued for PCT/JP2012/066761.

*Primary Examiner* — Bijan Ahvazi
*Assistant Examiner* — Ronald Grinsted
(74) *Attorney, Agent, or Firm* — Locke Lord LLP; James E. Armstrong, IV; Nicholas J. DiCeglie, Jr.

(57) ABSTRACT

The invention provides non-spherical resin particles with a novel shape capable of improving light diffusion, adhesion, oil absorption, and other properties, as well as a manufacturing method and use of the particles. Each non-spherical resin particle includes a concave portion and a convex portion formed in the concave portion, wherein the convex portion has a quasi-spherical surface. The method of manufacturing non-spherical resin particles involves a step of polymerizing 100 parts by weight of a first monomer mixture containing 77 to 99.99 parts by weight of a branched alkyl methacrylate, 0.01 to 3 parts by weight of a polyfunctional monomer, and 0 to 20 parts by weight of a monofunctional (meth)acrylate which is not a branched alkyl methacrylate, in the presence of 0.1 to 0.9 parts by weight of a chain transfer agent and 0 to 100 parts by weight of a (meth)acrylate polymer, to obtain resin particles.

9 Claims, 16 Drawing Sheets

(51) Int. Cl.
    *A61K 8/02*           (2006.01)
    *C08F 2/38*           (2006.01)
    *C08F 265/06*        (2006.01)
    *C08F 220/18*        (2006.01)
    *C08F 222/10*        (2006.01)

(52) U.S. Cl.
    CPC ............ *C08F 265/06* (2013.01); *C08L 47/00*
           (2013.01); *C08F 222/1006* (2013.01); *C08F*
                *2220/1833* (2013.01); *Y10T 428/2982*
                                        (2015.01)

(58) Field of Classification Search
    USPC .......................................... 252/582; 428/402
    See application file for complete search history.

(56) References Cited

FOREIGN PATENT DOCUMENTS

| | | | |
|---|---|---|---|
| JP | 2007105873 A | * | 4/2007 |
| JP | 2008-163171 A | | 7/2008 |
| JP | 2008-239967 A | | 10/2008 |
| JP | 2009-191236 A | | 8/2009 |
| JP | 2010-079318 A | | 4/2010 |
| JP | 2011-063758 A | | 3/2011 |
| WO | WO-2009/128441 A1 | | 10/2009 |
| WO | WO-2010/113812 A1 | | 10/2010 |

* cited by examiner

NON-SPHERICAL RESIN PARTICLES, MANUFACTURING METHOD THEREOF, AND USE THEREOF

TECHNICAL FIELD

The present invention relates to non-spherical resin particles for typical use as a light diffusing agent constituting light diffusers, such as light diffusion films, light diffusion plates, and LED light covers; a light diffusing agent constituting light diffusion coating agents, such as coating materials, paper coating agents, and light diffusing film coating agents; a light diffusing agent constituting anti-glare films; and an additive for cosmetics (slip enhancement agent). The present invention further relates to manufacturing methods and uses (for external preparations, coating materials, and light diffusion members) of the particles.

BACKGROUND ART

Non-spherical resin particles produced by seed polymerization are conventionally known. Comparative example 5 of Patent Document 1 and comparative example 1 of Patent Document 2 give examples that describe polymer particles shaped like a snowman.

Patent Document 3 describes cocoon-shaped polymer particles and discloses that the particles, when added to coating materials or cosmetics, effectively impart to them viscosity, light scattering, and other unique surface properties.

Patent Document 4 describes polymer particles with a recessed sectional shape having one notch part continued in the diameter direction, a mushroom shape, a semi-spherical shape, or a double-sided convex lens shape.

CITATION LIST

Patent Literature

Patent Document 1: Japanese Patent Application Publication, Tokukaihei, No. 8-120005
Patent Document 2: Japanese Patent Application Publication, Tokukai, No. 2011-63758
Patent Document 3: Japanese Patent Application Publication, Tokukai, No. 2008-163171
Patent Document 4: PCT International Application Publication, No. WO2010/113812

SUMMARY OF THE INVENTION

Problems to be Solved by the Invention

Conventionally known non-spherical resin particles are limited to these shapes and not capable of delivering desired properties (for example, light diffusion, adhesion, and oil absorption properties), leaving room for further improvement. Non-spherical resin particles with a novel shape would exhibit enhanced light diffusion, adhesion, oil absorption, and other properties.

It is an object of the present invention to provide non-spherical resin particles with a novel shape capable of improving light diffusion, adhesion, oil absorption, and other properties, as well as to provide a manufacturing method and use (for an external preparation, a coating material, and a light diffusion member) of the particles.

Solution to Problems

Non-spherical resin particles of the present invention each include a concave portion and a convex portion formed in the concave portion, wherein the convex portion has a quasi-spherical surface.

The non-spherical resin particles structured as above achieve advantageous effects in various uses because they include a concave portion and a convex portion formed in the concave portion, and have a large specific surface area. For example, if non-spherical resin particles with a large specific surface area are mixed with a binder (adhesive) to produce a coating agent (for optical film or similar use), the particles contact the binder in increased area, exhibiting improved adhesion to the binder. When the resultant coating agent is applied to a surface, the particles will less likely come off from the surface. Alternatively, if non-spherical resin particles with a large specific surface area are added to a cosmetic, the particles increase the oil absorption by the cosmetic, imparting improved oil absorption properties to the cosmetic. Another example is an application of non-spherical resin particles with a large specific surface area to a light diffusing agent constituting a light diffuser, such as a diffusion film, a diffusion plate, or an LED light cover. The non-spherical resin particles will have an increased interface (with another material) where light is refracted or reflected, achieving improved light diffusion.

The non-spherical resin particles structured as above are highly light-refractive because the convex portion of each particle has a quasi-spherical surface. The particles therefore exhibits improved light diffusion when applied to a light diffusing agent constituting a light diffuser, such as a diffusion film, a diffusion plate, or an LED light cover. In addition, the non-spherical resin particles structured as above have reduced frictional resistance on their surfaces because the convex portion of each particle has a quasi-spherical surface. The particles therefore provide improved touch feeling when added to a cosmetic.

The non-spherical resin particles of the present invention improve light diffusion, adhesion, oil absorption, and other properties as detailed above.

A method of manufacturing non-spherical resin particles of the present invention involves the first step of polymerizing 100 parts by weight of a first monomer mixture containing 77 to 99.99 parts by weight of a branched alkyl methacrylate, 0.01 to 3 parts by weight of a polyfunctional monomer, and 0 to 20 parts by weight of a monofunctional (meth)acrylate which is not a branched alkyl methacrylate, in the presence of 0.1 to 0.9 parts by weight of a chain transfer agent and 0 to 100 parts by weight of a (meth) acrylate polymer, to obtain resin particles, and the second step of letting the obtained resin particles to absorb a second monomer mixture containing a monofunctional aliphatic monomer and a polyfunctional monomer, and thereafter polymerizing the resin particles, wherein in the second step, the polyfunctional monomer is used in an amount of from 5 to 50 wt % to the amount of the monofunctional aliphatic monomer being used.

According to the method, 100 parts by weight of a first monomer mixture containing at least 77 wt % branched alkyl methacrylate (a monomer of a relatively low solubility parameter value (SP value)) and containing at least 97 wt % monofunctional (meth)acrylate (a branched alkyl methacrylate and a monofunctional (meth)acrylate which is not a branched alkyl methacrylate) is polymerized in the presence of a maximum of 100 parts by weight of a (meth)acrylate polymer. The resin particles obtained from the polymerization have a low solubility parameter value, hence a large difference in solubility parameter value from the second monomer mixture. That helps the second monomer mixture absorbed by the resin particles phase-separate from the resin particles.

According to the method, the resin particles are obtained from polymerization of the first monomer mixture containing at least 0.01 wt % polyfunctional monomer. The obtained resin particles are therefore a polymer sufficiently exhibiting properties of crosslinked structure. That helps the second monomer mixture absorbed by the resin particles phase-separate from the resin particles and enables the resin particles to better maintain their shape. Also, according to the method, the resin particles are obtained from polymerization of the first monomer mixture containing a maximum of 3 wt % polyfunctional monomer. The obtained resin particles are therefore a polymer with a crosslinked structure of a relatively low degree of crosslinking. That enables the second monomer mixture to be sufficiently absorbed by the resin particles.

According to the method, the first monomer mixture is polymerized in the presence of a maximum of 0.9 parts by weight of a chain transfer agent to 100 parts by weight of the first monomer mixture. The resin particles obtained from the polymerization therefore do not have too short a molecular chain, thus better maintaining their shape. Also, according to the method, the first monomer mixture is polymerized in the presence of a minimum of 0.1 parts by weight of a chain transfer agent to 100 parts by weight of the first monomer mixture. The resin particles obtained from the polymerization therefore do not have too long a molecular chain, thus enabling the second monomer mixture to be sufficiently absorbed by the resin particles.

According to the method, in the second step, the polyfunctional monomer is used in an amount of from 5 to 50 wt % to the amount of the monofunctional aliphatic monomer being used. That would help the polymerized second monomer mixture phase-separate from the resin particles.

As described in the foregoing, according to the method, when the resin particles are let to absorb the second monomer mixture, the resin particles sufficiently absorb the second monomer mixture, the second monomer mixture and its polymer relatively easily phase-separate from the resin particles, and the resin particles better maintain their shape. Due to synergistic effects of these phenomena, the second monomer mixture forms a shell with a local opening produced by phase separation so that the convex portion, originating from the resin particle's sphere, can remain exposed. The non-spherical resin particles of the present invention are hence obtained which each include a concave portion and a convex portion formed in the concave portion, wherein the convex portion has a quasi-spherical surface.

Furthermore, according to the method, the second monomer mixture containing a monofunctional aliphatic monomer and a polyfunctional monomer is absorbed by the resin particles (i.e., crosslinked seed particles) obtained from the polymerization of the first monomer mixture containing a branched alkyl methacrylate and a polyfunctional monomer before the second monomer mixture is polymerized. Accordingly, in comparison with a method whereby a monomer is absorbed by non-crosslinked seed particles before seed polymerization as described in examples 1 to 17 in Patent Document 4, the present method produces non-spherical resin particles with a relatively high degree of crosslinking in the portion originating from the seed particles. The method therefore produces non-spherical resin particles which reduce bleedout and elution of the portion originating from the seed particles when the particles are put into a solvent. The reduced elution will result in less elution-induced viscosity increase when the particles are mixed with a solvent to obtain a coating agent. That in turn will lead to ease of coating and uniformity in coats. The reduced elution will result in less elution-induced non-uniformity of a coat when the particles are mixed with a solvent to obtain a coating agent. The method also produces non-spherical resin particles which, allowing less components to elute in a solvent, exhibit improved properties and high resistance to solvent in other uses, for example, when the particles are used in mold products and cosmetics. The non-spherical resin particles obtained by the method therefore possess advantageous properties in a wide range of uses.

Throughout this specification, "(meth)acrylic" means either "acrylic" or "methacrylic," and "(meth)acrylate" means either "acrylate" or "methacrylate."

Note that the non-spherical resin particles with the unique shape produced by the present invention are not obtainable by the particle manufacturing methods of Patent Documents 1 to 4.

First, according to the particle manufacturing method of Patent Document 1, a monomer and a crosslinking agent are supplied uniformly to seed polymerization active sites as described in paragraph [0013] of Patent Document 1, The obtained polymer particles are therefore spherical. Similarly, according to the particle manufacturing method described in claim 5 of Patent Document 2, the obtained polymer particles are spherical as described in paragraph [0009] of Patent Document 2.

According to the particle manufacturing method described in comparative example 5 of Patent Document 1 and the particle manufacturing method described in comparative example 1 of Patent Document 2, the resin particles obtained from copolymerization of methyl methacrylate and a crosslinked monomer are let to absorb a monomer before seed polymerization. The obtained resin particles are all non-spherical and uniformly shaped like a snowman because the phase separation between the seed particles and the monomer is more difficult to occur by this conventional method than by the method of the present invention whereby the resin particles obtained from polymerization of the first monomer mixture containing a branched alkyl methacrylate and a polyfunctional monomer are let to absorb a monomer before seed polymerization.

According to the particle manufacturing method described in claims of Patent Document 3, the resin particles obtained from copolymerization of methyl methacrylate, a crosslinked monomer, etc. are let to absorb a monomer before seed polymerization. The obtained resin particles are all non-spherical and uniformly shaped like a cocoon because phase separation between the seed particles and the monomer is more difficult to occur by this conventional method than by the method of the present invention whereby the resin particles obtained from polymerization of the first monomer mixture containing a branched alkyl methacrylate and a polyfunctional monomer are let to absorb a monomer before seed polymerization.

According to the particle manufacturing method described in examples 1 to 17 of Patent Document 4, non-crosslinked seed particles are let to absorb a monomer before seed polymerization. The obtained resin particles are all non-spherical and have a recessed sectional shape having one notch part continued in the diameter direction, a mushroom shape, a semi-spherical shape, or a double-sided convex lens shape because the convex portion originating from the seed particle's sphere is more difficult to form on the surface by this conventional method than by the method of the present invention whereby the resin particles (i.e., crosslinked seed particles) obtained from polymerization of the first monomer mixture containing a branched alkyl methacrylate and a polyfunctional monomer are let to absorb a monomer before seed polymerization.

An external preparation of the present invention contains non-spherical resin particles of the present invention. The external preparation of the present invention exhibits excellent moisture retention because it contains non-spherical resin particles of the present invention which exhibit excellent oil absorption properties.

A coating material of the present invention contains non-spherical resin particles of the present invention. The coating material of the present invention exhibits excellent scratch resistance because it contains non-spherical resin particles of the present invention which exhibit excellent adhesion to the binder.

A light diffusion member of the present invention contains non-spherical resin particles of the present invention. The light diffusion member of the present invention exhibits excellent light diffusion because it contains non-spherical resin particles of the present invention which have a large specific surface area and are hence highly light-refractive.

Advantageous Effects of the Invention

As described in the foregoing, the present invention produces non-spherical resin particles with a novel shape capable of improving light diffusion, adhesion, oil absorption, and other properties, as well as provides a manufacturing method and use (for an external preparation, a coating material, and a light diffusion member) of the particles.

DESCRIPTION OF EMBODIMENTS

The following will describe the present invention in detail.

Non-Spherical Resin Particles

Non-spherical resin particles of the present invention each include a concave portion (depression) and a convex portion formed in the concave portion, wherein the convex portion has a quasi-spherical surface.

Figure 1:
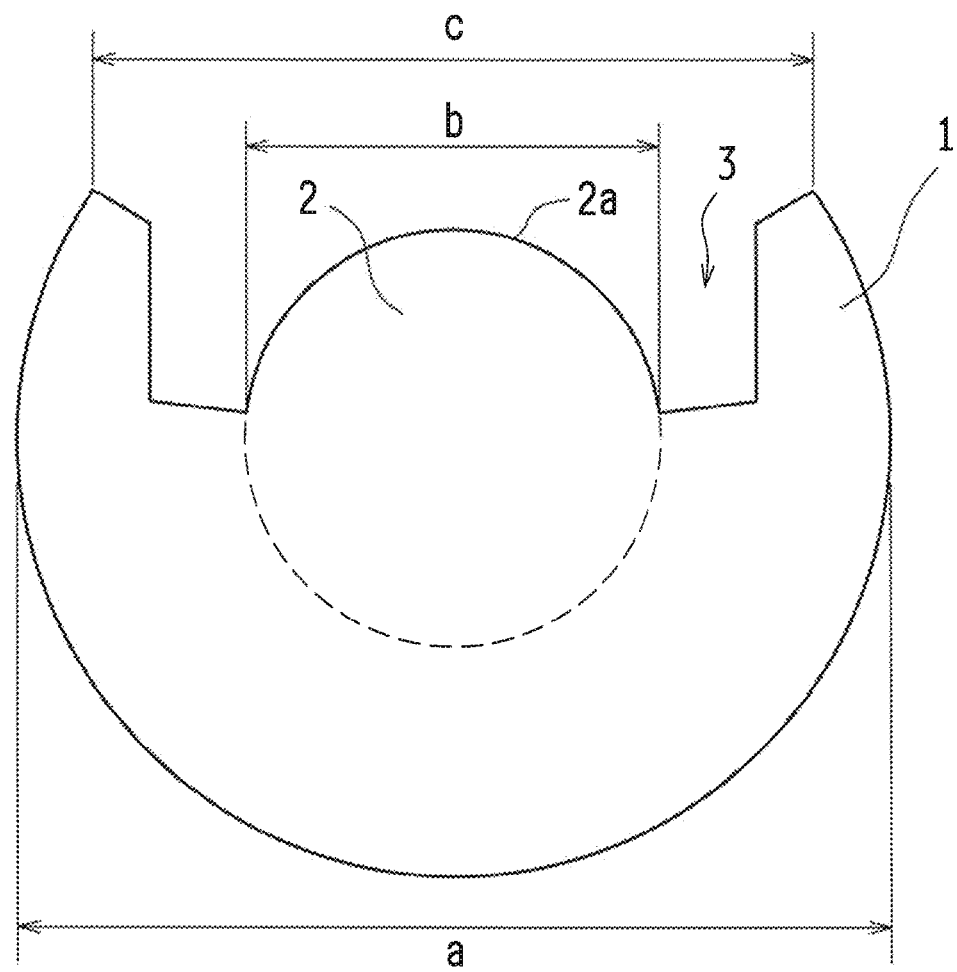
FIG. 1 is a schematic cross-sectional view of a non-spherical resin particle in accordance with an example of the present invention.
Figure 2:
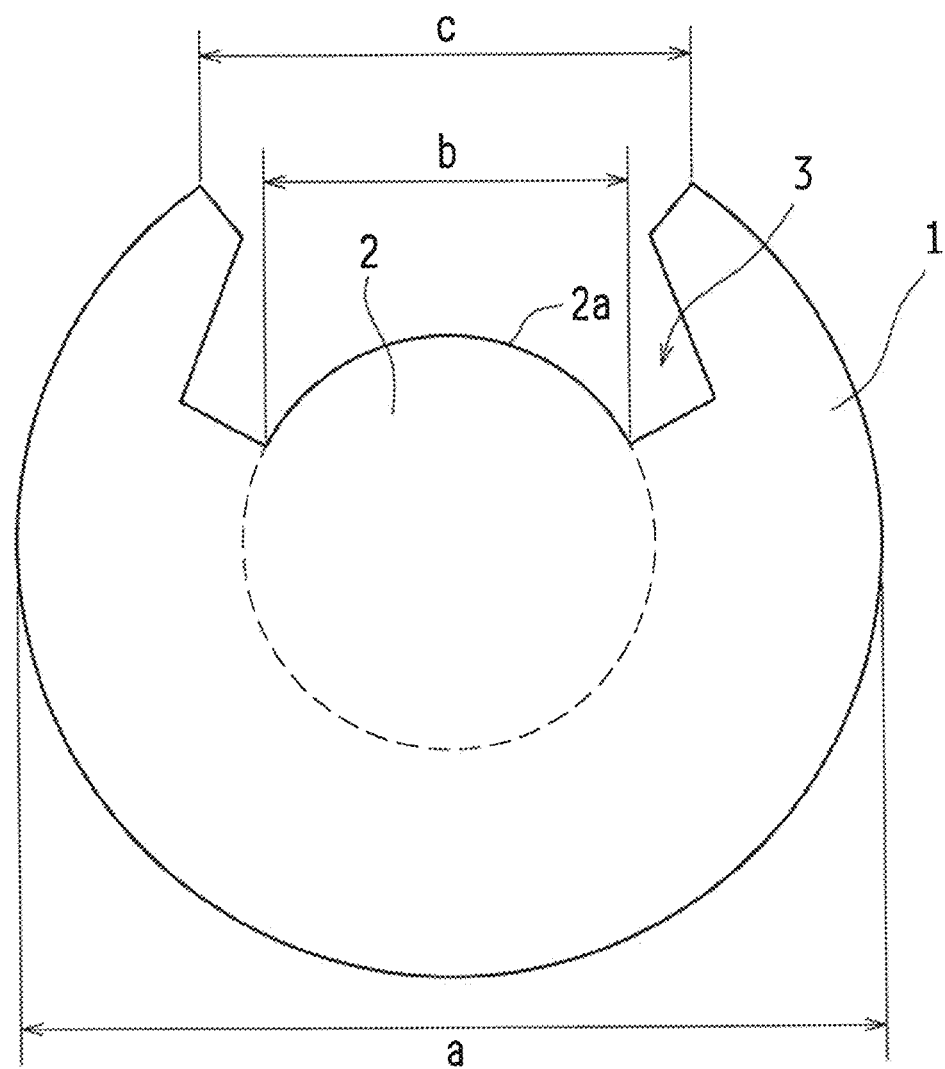
FIG. 2 is a schematic cross-sectional view of a non-spherical resin particle in accordance with another example of the present invention.

The shape of the non-spherical resin particle of the present invention will now be described in more detail in reference to FIGS. 1 and 2. The non-spherical resin particle of the present invention has, as shown in FIGS. 1 and 2, a spherical shell 1 and an inner core 2 formed contiguous to the shell 1 inside the shell 1 (closer to the center of the non-spherical resin particle). For example, the shell 1 has a local opening to expose a part of the surface of the inner core 2. The exposed part of the surface of the inner core 2 is a spherical convex surface 2a. In other words, for example, as shown in FIGS. 1 and 2, the non-spherical resin particle of the present invention has, in that single particle, a single concave portion (i.e., the combination of the inner core 2 and a hollow section 3 which will be detailed later) and a single convex portion (i.e., the inner core 2) formed in the concave portion, wherein the convex portion has a surface which is the spherical convex surface 2a, and the non-concave portion (i.e., the shell 1) of the non-spherical resin particle has a spherical surface. A cavity is preferably formed between the shell 1 and the inner core 2 as illustrated in FIGS. 1 and 2.

The non-spherical resin particle of the present invention has a diameter ratio, b/a, (representative of the relative size of the inner core 2) in the range of preferably 0.25 to 0.70 and more preferably 0.25 to 0.50, where "a" is the diameter of the non-spherical resin particle (diameter of the shell 1), and "b" is the diameter of the convex portion (diameter of the convex surface 2a). If the ratio, b/a, is 0.25 or greater, the convex portion is large enough to achieve expected effects of the convex portion with a quasi-spherical surface: specifically, light diffusion, adhesion, oil absorption, and other properties are sufficiently improved. If the ratio, b/a, is 0.70 or less, the non-spherical resin particle, taken in its entirety has a shape far from a sphere and is for this reason capable of improving light diffusion, adhesion, oil absorption, and other properties. The ratio, b/a, may be adjusted by changing the composition of the non-spherical resin particle.

The non-spherical resin particle of the present invention has a diameter ratio, c/a, (representative of the proportion of the opening in the shell 1) of preferably at least 0.20 and more preferably from 0.20 inclusive to 0.60 inclusive, where "a" is the diameter of the non-spherical resin particle (diameter of the shell 1), and "c" is the diameter of the concave portion (diameter of the opening in the shell 1). If the ratio, c/a, is 0.20 or greater, the non-spherical resin particle, taken in its entirety, has a shape far from a sphere and is for this reason capable of improving light diffusion, adhesion, oil absorption, and other properties. If the ratio, c/a, is 0.60 or less, the concave portion is large enough to achieve expected effects of the concave portion: specifically, light diffusion, adhesion, oil absorption, and other properties are sufficiently improved. The ratio, c/a, never exceeds 1.00 because the diameter of the concave portion is never greater than the diameter of the non-spherical resin particle. The ratio, c/a, may be adjusted by changing the composition of the non-spherical resin particle.

In the examples shown in FIGS. 1 and 2, the surface of the non-concave portion of the non-spherical resin particle is depicted as a smooth spherical surface (convex surface). The surface of the non-concave portion of the non-spherical resin particle of the present invention (shell 1) preferably has a roughness smaller than the convex and concave portions. In other words, the surface of the non-concave portion of the non-spherical resin particle of the present invention (shell 1) preferably has second concave portions smaller than the concave portion. Accordingly, the specific surface area of the non-spherical resin particle is larger than that of a particle without the small roughness and for this reason capable of achieving advantageous effects in various uses. For example, if non-spherical resin particles with a large specific surface area are mixed with a binder to produce a coating agent, the particles contact the binder in increased area, exhibiting improved adhesion to the binder. When the resultant coating agent is applied to a surface, the non-spherical resin particles will less likely come off from the surface. The small roughness do not exist on the surface of the non-spherical resin particles of Patent Document 4. The small roughness is a unique feature of the non-spherical resin particles obtained by the method of the present invention in which crosslinked seed particles are used.

The second concave portions on the surface of the non-concave portion (shell 1) of the non-spherical resin particle of the present invention preferably have a maximum depth of greater than or equal to 50 nm. If the second concave portions have a maximum depth of less than 50 nm, the small roughness do not provide a sufficient increase in the specific surface area of the non-spherical resin particle. Therefore, for example, if the non-spherical resin particles are mixed with a binder to produce a coating agent, the particles do not sufficiently improve adhesion to the binder. In addition, the second concave portions on the surface of the non-concave portion (shell 1) of the non-spherical resin particle of the present invention preferably have a maximum depth of less than or equal to 500 nm. If the second concave portions have a maximum depth in excess of 500 nm, the non-spherical resin particle has a shape that is far from a sphere, which would result in undesirable disbenefits, for example, poor slippage in cosmetics. In addition, under the same condition, the roughness is excessively large so that too much of incoming light is reflected by the surface of the non-spherical resin particle. That decreases the total light transmittance of the non-spherical resin particle. Throughout the present application, the maximum depth of second concave portions is calculated from a TEM or SEM image of the non-spherical resin particle by the method described in an example of the invention.

The shell 1 and the inner core 2 are made preferably of a polymer of a vinyl-based monomer, more preferably a polymer of a vinyl-based monomer containing 50 wt % or more (meth)acrylate, even more preferably a polymer of a vinyl-based monomer containing 50 wt % or more alkyl (meth)acrylate.

In these cases, if the non-spherical resin particles are mixed with a binder to produce a coating agent, the particles are compatibly mixed with the binder, which increases the adhesive strength of the particles to the binder. When the resultant coating agent is applied to a surface, the particles will less likely come off from the surface. On the other hand, if either the shell 1 or the inner core 2 is not a polymer of a vinyl-based monomer (for example, if the shell 1 is a polymer of a vinyl-based monomer, and the inner core 2 is made of a silicone resin) and if the non-spherical resin particles are mixed with a binder to produce a coating agent, the particles are not compatibly mixed with the binder, which decreases the adhesive strength of the particles to the binder. When the resultant coating agent is applied to a surface, the particles will likely come off from the surface.

If both the shell 1 and the inner core 2 are made of a polymer of a vinyl-based monomer containing 50 wt % or more acrylate, especially if both the shell 1 and the inner core 2 are made of a polymer of a vinyl-based monomer containing 50 wt % or more alkyl (meth)acrylate, the shell 1 and the inner core 2 hardly differ in refractive index. The very small refractive index difference reduces light scattering at the interface of the shell 1 and the inner core 2, increasing the total light transmittance of the non-spherical resin particles. On the other hand, if the shell 1 is a polymer of a vinyl-based monomer containing 50 wt % or more (meth)acrylate, and the inner core 2 is made of a silicone resin, the shell 1 and the inner core 2 differ significantly in refractive index. The relatively large difference increases light diffusion by the particles, decreasing the total light transmittance of the particles.

The shell 1 and the inner core 2 preferably have a difference in refractive index of less than or equal to 0.05. If the shell 1 and the inner core 2 have a difference in refractive index of greater than 0.05, the non-spherical resin particles have a relatively low total light transmittance. That in turn results in, for example, a low total light transmittance of the light diffusion member when the particles are contained as a light diffusing agent in the light diffusion member. The light diffusion member containing the non-spherical resin particles preferably has a haze of greater than or equal to 80% and a total light transmittance of greater than or equal to 85%. In these cases, the resultant light diffusion member is excellent and exhibits good light diffusion and good optical transparency.

A "vinyl-based monomer" as used herein refers to a compound with one polymerizable alkenyl group (vinyl group in a broad sense of the term) per molecule.

Examples of the vinyl-based monomer may include (meth)acrylates; ethylenic unsaturated carboxylic acids, such as acrylic acid, methacrylic acid, maleic acid, and fumaric acid; α-haloacrylates, such as methyl αchloroacrylates; aromatic vinyl compounds, such as styrene, o-methylstyrene, m-methylstyrene, p-methylstyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene, 3,4-dichlorostyrene, vinyl naphthalene, and divinylbenzene; vinyl carboxylates, such as vinyl acetate, vinyl propionate, and vinyl butyrate; (meth)acrylate derivatives (except for (meth)acrylates), such as acrylonitriles, methacrylonitriles, and (meth)acrylamides; vinyl ethers, such as vinyl methyl ethers, vinyl ethyl ethers, and vinyl isobutyl ethers; vinyl ketones, such as vinyl methyl ketones, vinyl hexyl ketones, and methyl isopropenyl ketones; and N-vinyl compounds (e.g., N-vinyl amines and N-vinyl amides), such as N-vinylpyrrole, N-vinylcarbazole, N-vinylindole, and N-vinylpyrrolidone.

Examples of the (meth)acrylate may include alkyl (meth)acrylates, such as methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth)acrylate, n-heptyl (meth)acrylate, n-octyl (meth)acrylate, 2-ethylhexyl (meth)acrylate, n-nonyl (meth)acrylate, and n-decyl (meth)acrylate; cycloalkyl (meth)acrylates, such as cyclohexyl (meth)acrylate; monofunctional (meth)acrylates (except for alkyl (meth)acrylates), such as 2-hydroxylethyl (meth)acrylate, glycidyl (meth)acrylate, and (meth)acrylates with a alkylene oxide group (examples of (meth)acrylates with a alkylene oxide group will be described in detail in paragraphs under the heading, "Seed Polymerization Step"); and polyfunctional (meth)acrylates, such as ethylene glycol di(meth)acrylates and trimethylolpropane tri(meth)acrylates. Any one of these compounds may be used alone, or alternatively two or more of them may be used together in any combination. A "monofunctional (meth)acrylate" as used herein refers to a (meth)acrylate with one polymerizable alkenyl group (vinyl group in a broad sense of the term) per molecule. A "polyfunctional (meth)acrylate" as used herein refers to a (meth)acrylate with two or more polymerizable alkenyl group (vinyl group in a broad sense of the term) per molecule.

The non-spherical resin particles of the present invention preferably have diameters with a coefficient of variation of less than or equal to 15%. When this is the case, the particles have improved uniformity in their properties (from one particle to the other). Therefore, if the particles are used as a light diffusing agent to produce a light diffuser (e.g., a light diffusion film) or a cosmetic, the resultant light diffuser or cosmetic exhibits uniform optical properties.

The non-spherical resin particles of the present invention preferably have an average particle diameter in the range of 0.5 to 50 μm. When this is the case, the resultant particles are suited for various uses. If the particles are used as an element (light diffusing agent) for an anti-glare film, the particles more preferably have an average particle diameter in the range of 1.5 to 8 μm. When this is the case, the resultant anti-glare film exhibits good anti-glare properties. If the particles are used as an element (light diffusing agent) for a light diffusion film, the particles more preferably have an average particle diameter in the range of 1 to 50 μm and even more preferably have an average particle diameter in the range of 3 to 10 μm. When this is the case, the resultant light diffusion film exhibits good light diffusion. If the particles are used as an additive for a cosmetic, the particles preferably have an average particle diameter in the range of 1 to 50 μm. When this is the case, the resultant cosmetic is of high quality. If the particles are used as a paper coating agent, the particles preferably have an average particle diameter in the range of 0.5 to 10 μm. When this is the case, the resultant paper coating agent is of high quality. If the particles have an average particle diameter in the range of 1 to 10 μm, especially an average particle diameter of approximately 3 μm, the resultant particles are readily controllable in terms of their shape to achieve a desired non-spherical shape, which facilitates the manufacture of the particles.

Method of Manufacturing Non-Spherical Resin Particles

A method of manufacturing non-spherical resin particles in accordance with the present invention involves the first step of polymerizing 100 parts by weight of a first monomer mixture containing 77 to 99.99 parts by weight of a branched alkyl methacrylate, 0.01 to 3 parts by weight of a polyfunctional monomer, and 0 to 20 parts by weight of a monofunctional (meth)acrylate which is not a branched alkyl methacrylate, in the presence of 0.1 to 0.9 parts by weight of a chain transfer agent and 0 to 100 parts by weight of a (meth)acrylate polymer, to obtain resin particles, and the second step (seed polymerization step) of letting the obtained resin particles to absorb a second monomer mixture containing a monofunctional aliphatic monomer and a polyfunctional monomer, and thereafter polymerizing the resin particles, wherein in the second step, the polyfunctional monomer is used in an amount of from 5 to 50 wt % to the amount of the monofunctional aliphatic monomer being used. The method enables highly reliable manufacture of the non-spherical resin particles of the present invention.

Seed Particle Preparation Step

The first step produces resin particles (i.e., seed particles) for use to absorb the second monomer mixture in the seed polymerization step. In the first step, the first monomer mixture is polymerized in the presence of a chain transfer agent or in the presence of a chain transfer agent and a (meth)acrylate polymer to obtain seed particles.

The first monomer mixture contains at least a branched alkyl methacrylate and a polyfunctional monomer. The branched alkyl methacrylate may be, for example, isopropyl methacrylate, isobutyl methacrylate, tert-butyl methacrylate, 2-ethylhexyl methacrylate, or iso-octyl methacrylate. Any one of these compounds may be used alone, or alternatively two or more of them may be used together in any combination. The most preferable branched alkyl methacrylate is isobutyl methacrylate because of its low solubility parameter value and ease in inducing phase separation between the seed particles and the second monomer mixture to form a non-spherical shape unique to the present invention. The branched alkyl methacrylate is used in an amount of from 77 to 99.99 parts by weight to 100 parts by weight of the first monomer mixture and preferably from 90 to 99.9 parts by weight to 100 parts by weight of the first monomer mixture.

The polyfunctional monomer is a compound with two or more polymerizable alkenyl groups (vinyl groups in a broad sense of the term) per molecule. The polyfunctional monomer may be, for example, ethylene glycol di(meth)acrylate, propylene glycol di(meth)acrylate, triethylene glycol di(meth)acrylate, trimethylolpropane tri(meth)acrylate, pentaerythritol tetra(meth)acrylate, or divinylbenzene. The polyfunctional monomer preferably does not have a divalent straight-chain hydrocarbon group with four or more carbon atoms between polymerizable alkenyl groups. If the polyfunctional monomer has a divalent straight-chain hydrocarbon group with four or more carbon atoms between polymerizable alkenyl groups, the phase separation between the seed particles and the second monomer mixture becomes difficult to take place, making it less likely to obtain a non-spherical shape unique to the present invention. This is not desirable. The polyfunctional monomer is used in an amount of from 0.01 to 3 parts by weight to 100 parts by weight of the first monomer mixture and preferably from 0.1 to 3 parts by weight to 100 parts by weight of the first monomer mixture. The use of the polyfunctional monomer in a quality greater than or equal to 0.1 parts by weight to 100 parts by weight of the first monomer mixture further facilitates the phase separation between the seed particles and the second monomer mixture, making it more likely to obtain a non-spherical shape unique to the present invention. If the polyfunctional monomer is used in excess of 3 parts by weight to 100 parts by weight of the first monomer mixture, the seed particles are excessively crosslinked, which causes the seed particles to poorly absorb the second monomer mixture. Possibly, the seed particles would not absorb the second monomer mixture before polymerization. When that actually happens, fine particles are produced in such large numbers that the particle diameters have a large coefficient of variation (CV value). This is not desirable.

The first monomer mixture may contain a monofunctional (meth)acrylate which is not a branched alkyl methacrylate in an amount of less than or equal to 20 parts by weight, more preferably less than or equal to 10 parts by weight, to 100 parts by weight of the first monomer mixture. The monofunctional (meth)acrylate which is not a branched alkyl methacrylate may be, for example, methyl (meth)acrylate, ethyl (meth)acrylate, n-propyl (meth)acrylate, isopropyl acrylate, n-butyl (meth)acrylate, isobutyl acrylate, tert-butyl acrylate, n-pentyl (meth)acrylate, n-hexyl (meth)acrylate, n-heptyl (meth)acrylate, n-octyl (meth)acrylate, 2-ethylhexyl acrylate, n-nonyl (meth)acrylate, n-decyl (meth)acrylate, or cyclohexyl (meth)acrylate. Any one of these compounds may be used alone, or alternatively two or more of them may be used together in any combination.

The chain transfer agent may be, for example, a mercaptan, such as n-octyl mercaptan or tert-dodecyl mercaptan; an α-methylstyrene dimer; a terpene, such as γ-terpinene or dipentene; or a halogenated hydrocarbon, such as chloroform or carbon tetrachloride. The chain transfer agent is preferably a mercaptan and especially preferably n-octyl mercaptan. The chain transfer agent is used in an amount of from 0.1 to 0.9 parts by weight to 100 parts by weight of the first monomer mixture and preferably from 0.1 to 0.5 parts by weight to 100 parts by weight of the first monomer mixture. If the chain transfer agent is used in an amount of less than or equal to 0.5 parts by weight to 100 parts by weight of the first monomer mixture, the seed particles have a longer molecular chain. That further facilitates the phase separation between the seed particles and the second monomer mixture, making it more likely to obtain a non-spherical shape unique to the present invention. On the other hand, if the chain transfer agent is used in an amount of less than 0.1 parts by weight, the seed particles have too large a molecular weight, which disrupts absorption.

In the first step, the first monomer mixture may be polymerized in the presence of a chain transfer agent by emulsion polymerization, suspension polymerization, or any other publicly known method, to obtain seed particles. Among these methods, emulsion polymerization is preferred considering its simplicity and convenience and the uniform particle diameters of resultant seed particles. The following will describe a method based on emulsion polymerization; the invention is however by no means limited to that method.

If the first monomer mixture is to be emulsion-polymerized in the presence of a chain transfer agent to obtain resin particles, first, the first monomer mixture and chain transfer agent are dispersed in an aqueous medium to prepare an aqueous emulsion.

The aqueous medium may be, for example, water or a mixed medium of water and a water soluble solvent (e.g., lower alcohol (alcohol with 5 or less carbon atoms)). A surfactant (described later in detail under the heading, "Seed Polymerization Step") may be or may not be added to the aqueous medium. The first monomer mixture is added to the aqueous medium and dispersed in the aqueous medium using a fine emulsifier, such as a main stirrer, a homogenizer, an ultrasonic processor, or a nanomizer, to prepare a dispersion liquid which is then heated to polymerization temperature. After the reaction system is purged (replaced) by nitrogen or a like inert gas, the whole mixture is polymerized while gradually adding an aqueous solution of a polymerization initiator dropwise to the dispersion liquid, to obtain seed particles.

Examples of the polymerization initiator may include persulfates, such as potassium persulfate, ammonium persulfate, and sodium persulfate; organic peroxides, such as benzoyl peroxide, lauroyl peroxide, orthochlorobenzoyl peroxide, orthomethoxybenzoyl peroxide, 3,5,5-trimethylhexanoyl peroxide, tert-butyl peroxy-2-ethylhexanoate, and di-tert-butyl peroxide; and azo-based compounds, such as 2,2'-azobisisobutyronitrile, 1,1'-azobiscyclohexanecarbonitrile, and 2,2'-azobis(2,4-dimethylvaleronitrile). The polymerization initiator is preferably used in an amount of from 0.1 to 3 parts by weight to 100 parts by weight of the first monomer mixture.

Next, the first monomer mixture in the aqueous emulsion is polymerized to obtain seed particles. The polymerization temperature may be selected as appropriate according to the type of the first monomer mixture and that of the polymerization initiator. The polymerization temperature is preferably 25 to 110° C. and more preferably 50 to 100° C. After completion of the polymerization, if necessary, the seed particles may be separated out from the aqueous medium by, for example, filtering, the aqueous medium may be removed from the seed particles by, for example, centrifugation, and the seed particles may be washed in water and a solvent before being dried.

In this manner, seed particles are obtained by polymerization in the presence of a chain transfer agent.

If the first monomer mixture is polymerized in the presence of a chain transfer agent and a (meth)acrylate polymer in the first step to obtain seed particles, the (meth)acrylate polymer is used in an amount of less than or equal to 100 parts by weight, preferably in an amount of greater than or equal to 1 part by weight and less than or equal to 80 parts by weight, to 100 parts by weight of the first monomer mixture. The use of the (meth)acrylate polymer in an amount of less than or equal to 80 parts by weight to 100 parts by weight of the first monomer mixture facilitates the phase separation between the seed particles and the second monomer mixture, making it more likely to obtain a non-spherical shape unique to the present invention. The use of the (meth)acrylate polymer in that amount also enables a sufficient increase of the particle diameter during the polymerization. Productivity is thus improved. Meanwhile, the use of the (meth)acrylate polymer in an amount of greater than or equal to 1 part by weight to 100 parts by weight of the first monomer mixture prevents the first monomer mixture from being suspension-polymerized alone (without being absorbed by the seed particles) in the aqueous medium to form abnormal particles.

In that case, a seed polymerization process is preferably used whereby a (meth)acrylate is polymerized to obtain (meth)acrylate polymer particles before letting the obtained (meth)acrylate polymer particles to absorb a first monomer mixture containing a branched alkyl methacrylate and a polyfunctional monomer and polymerizing the resultant particles in the presence of a chain transfer agent. The method of preparing the (meth)acrylate polymer particles will be described later in detail.

According to this seed polymerization process, first, a first monomer mixture and a chain transfer agent are dispersed in an aqueous medium to obtain an aqueous emulsion, and (meth)acrylate polymer particles are added as seed particles to the aqueous emulsion. The aqueous medium may be one of the media listed above. A surfactant (described later in detail under the heading, "Seed Polymerization Step") may be added to the aqueous medium. The aqueous emulsion may be prepared by, for example, a method using a fine emulsifier mentioned above.

The first monomer mixture may be mixed with a polymerization initiator mentioned above when necessary. The polymerization initiator may be dispersed in the aqueous medium after being mixed with the first monomer mixture in advance. Alternatively, both the polymerization initiator and the first monomer mixture may be individually dispersed in an aqueous medium before they are mixed. Droplets of the first monomer mixture in the obtained aqueous emulsion preferably have smaller particle diameters than the (meth) acrylate polymer particles so that the first monomer mixture can be efficiently absorbed by the (meth)acrylate polymer particles. The polymerization initiator is preferably used in an amount of from 0.1 to 3 parts by weight to 100 parts by weight of the first monomer mixture.

The (meth)acrylate polymer particles may be directly added to the aqueous emulsion. Alternatively, the (meth) acrylate polymer particles may be dispersed in an aqueous medium before being added to the aqueous emulsion. After the (meth)acrylate polymer particles are added to the aqueous emulsion, the (meth)acrylate polymer particles are let to absorb the first monomer mixture. The absorption generally takes place by stirring the aqueous emulsion to which the (meth)acrylate polymer particles have been added, at room temperature (about 20° C.) for 1 to 12 hours. The absorption may be facilitated by heating the aqueous emulsion to about 30 to 50° C.

The (meth)acrylate polymer particles swell by absorbing the first monomer mixture. Completion of the absorption is determined by observing the growth of the particle diameter under an optical microscopic observation.

Next, the first monomer mixture absorbed by the (meth) acrylate polymer particles is polymerized to obtain seed particles. The polymerization temperature may be selected as appropriate according to the type of the first monomer mixture and that of the polymerization initiator. The polymerization temperature is preferably from 25 to 110° C. and more preferably from 50 to 100° C. The polymerization reaction is preferably carried out at elevated temperature after the (meth)acrylate polymer particles have completely absorbed the first monomer mixture. After completion of the polymerization, if necessary, the seed particles may be separated out from the aqueous medium by, for example, filtering, the aqueous medium may be removed from the seed particles by, for example, centrifugation, and the seed particles may be washed in water and a solvent before being dried.

In this manner, seed particles are obtained by polymerization in the presence of a chain transfer agent and (meth) acrylate polymer particles. The seed particles are not limited in any particular manner in terms of their size and shape. Generally, spherical seed particles with an average particle diameter of 0.1 to 5 µm are used.

Method of Preparing (Meth)Acrylate Polymer Particles

Next will be described a method of preparing (meth) acrylate polymer particles used as needed in the seed particle preparation step.

(Meth)acrylate is polymerized in this method of preparing (meth)acrylate polymer particles. The (meth)acrylate may be, methyl (meth)acrylate, ethyl (meth)acrylate, n-propyl (meth)acrylate, isopropyl (meth)acrylate, n-butyl (meth) acrylate, isobutyl (meth)acrylate, tert-butyl (meth)acrylate, n-pentyl (meth)acrylate, n-hexyl (meth)acrylate, n-heptyl (meth)acrylate, n-octyl (meth)acrylate, 2-ethylhexyl (meth) acrylate, n-nonyl (meth)acrylate, n-decyl (meth)acrylate, or cyclohexyl (meth)acrylate. Any one of these compounds may be used alone, or alternatively two or more of them may be used together in any combination. The (meth)acrylate may be the same compound as the branched alkyl methacrylate contained in the first monomer mixture.

The (meth)acrylate may be polymerized by emulsion polymerization, suspension polymerization, or any other publicly known method. Among these methods, emulsion polymerization is preferred considering its simplicity and convenience and the uniform particle diameters of resultant (meth)acrylate polymer particles. The following will describe an emulsion polymerization-based method; the present invention is however by no means limited to that method.

To emulsion-polymerize a (meth)acrylate to obtain (meth) acrylate polymer particles, first, the (meth)acrylate and a chain transfer agent are dispersed in an aqueous medium to prepare an aqueous emulsion.

The aqueous medium may be, for example, a medium mentioned above. A surfactant (described later in detail under the heading, "Seed Polymerization Step") may be added to the aqueous medium. The aqueous emulsion may be prepared by, for example, a method using a fine emulsifier mentioned above.

The (meth)acrylate may be mixed with a polymerization initiator mentioned above when necessary. The polymerization initiator may be dispersed in an aqueous medium after being mixed with the (meth)acrylate in advance. Alternatively, both the polymerization initiator and the (meth) acrylate may be individually dispersed in an aqueous medium before they are mixed. The polymerization initiator is preferably used in an amount of from 0.1 to 3 parts by weight to 100 parts by weight of the (meth)acrylate.

The polymerization of the (meth)acrylate is preferably carried out in the presence of a chain transfer agent mentioned above. The chain transfer agent is preferably a mercaptan and more preferably n-octyl mercaptan. The chain transfer agent is preferably used in an amount of from 0.1 to 0.9 parts by weight to 100 parts by weight of the (meth)acrylate and more preferably in an amount of from 0.1 to 0.5 parts by weight to 100 parts by weight of the (meth)acrylate. The use in these particular amounts facilitates the phase separation between the seed particles and the second monomer mixture, making it more likely to obtain a non-spherical shape unique to the present invention.

Next, the (meth)acrylate in the aqueous emulsion is polymerized to obtain (meth)acrylate polymer particles. The polymerization temperature may be selected as appropriate according to the type of the (meth)acrylate and that of the polymerization initiator. The polymerization temperature is preferably from 25 to 110° C. and more preferably from 50 to 100° C. After completion of the polymerization, the (meth)acrylate polymer particles are separated out from the aqueous medium by, for example, filtering, the aqueous medium may, if necessary, be removed from the (meth)

acrylate polymer particles by, for example, centrifugation, and the (meth)acrylate polymer particles may, if necessary, be washed in water and a solvent before being dried.

(Meth)acrylate polymer particles are hence obtained. The (meth)acrylate polymer particles are not limited in any particular manner in terms of size and shape. Generally, spherical (meth)acrylate polymer particles with particle diameters of 0.1 to 5 μm are used.

Seed Polymerization Step

In the seed polymerization step (second step), a second monomer mixture containing a monofunctional aliphatic monomer and a polyfunctional monomer is polymerized after being absorbed by resin particles, to obtain non-spherical resin particles.

A monofunctional aliphatic monomer is an aliphatic compound with one polymerizable alkenyl group (vinyl group in a broad sense of the term) per molecule. The monofunctional aliphatic monomer may be, for example, (meth)acrylic acid; a (meth)acrylate, such as methyl (meth)acrylate, ethyl (meth)acrylate, n-butyl (meth)acrylate, isobutyl (meth)acrylate, tert-butyl (meth)acrylate, 2-hydroxylethyl (meth)acrylate, glycidyl (meth)acrylate, or a (meth)acrylate with an alkylene oxide group; a (meth)acrylamide; a vinyl acetate; or an acrylonitrile. Any one of these monomers may be used alone, or alternatively two or more of them may be mixed for use. The monofunctional aliphatic monomer is preferably either a (meth)acrylate alone or a mixture a (meth)acrylate and another monofunctional aliphatic monomer and more preferably a (meth)acrylate alone.

The (meth)acrylate with an alkylene oxide group may be, for example, a compound of formula (1) below.

[Chem. 1]

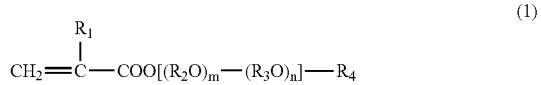

(1)

In the formula, $R_1$ is either H or $CH_3$; $R_2$ and $R_3$ each is independently an alkylene group selected from $C_2H_4$, $C_3H_6$, $C_4H_8$, and $C_5H_{10}$; m is from 0 to 50, and n is 0 from to 50 (not both of in and n are 0); and $R_4$ is either H or $CH_3$. If either or both of in and n is/are greater than 50 in the monomer of formula (1), the stability of polymerization may fall, causing stuck particles to form. In the formula, in and n are preferably in the range of 0 to 30 and more preferably in the range of 0 to 15.

The (meth)acrylate with an alkylene oxide group may be, for example, a Blemmer® series manufactured by NOF Corporation: e.g., Blemmer® 50 PEP-300 ($R_1$ is $CH_3$, $R_2$ is $C_2H_5$, $R_3$ is $C_3H_6$, m and n are respectively 3.5 and 2.5 on average (mixture), and $R_4$ is H), Blemmer® 70 PEP-350B ($R_1$ is $CH_3$, $R_2$ is $C_2H_5$, $R_3$ is $C_3H_6$, in and n are respectively 3.5 and 2.5 on average (mixture), and $R_4$ is H), Blemmer® PP-1000 ($R_1$ is $CH_3$, $R_3$ is $C_3H_6$, m is 0, n is 4 to 6 on average (mixture), and $R_4$ is H), and Blemmer® PME-400 ($R_1$ is $CH_3$, $R_2$ is $C_2H_5$, m is 9 on average (mixture), n is 0, and $R_4$ is $CH_3$).

The polyfunctional monomer is a compound with two or more polymerizable alkenyl groups (vinyl groups in a broad sense of the term) per molecule. The polyfunctional monomer may be, for example, ethylene glycol di(meth)acrylate, trimethylolpropane tri(meth)acrylate, or divinylbenzene. The polyfunctional monomer is used in an amount of from 5 to 50 parts by weight to 100 parts by weight of the monofunctional aliphatic monomer being used, and preferably in an amount of from 20 to 50 parts by weight to 100 parts by weight of the monofunctional aliphatic monomer being used. The use of the polyfunctional monomer in an amount of greater than or equal to 20 parts by weight to 100 parts by weight of the monofunctional aliphatic monomer being used would facilitate the phase separation between the seed particles and the second monomer mixture, making it more likely to obtain a non-spherical shape unique to the present invention.

In the seed polymerization step, the second monomer mixture is dispersed in an aqueous medium to prepare an aqueous emulsion. The aqueous medium may be, for example, a medium mentioned above. The aqueous emulsion may be prepared by, for example, the aforementioned method using fine emulsifier.

The aqueous emulsion preferably contains a surfactant. The surfactant may be any one of anionic surfactants, cationic surfactants, non-ionic surfactants, and amphoteric surfactants.

The anionic surfactant may be, for example, sodium oleate; a fatty acid oil, such as castor oil potash; an alkyl sulfate salt, such as sodium lauryl sulfate or ammonium lauryl sulfate; an alkylbenzenesulfonate, such as sodium dodecylbenzenesulfonate; an alkylnaphthalenesulfonate; an alkanesulfonate; a dialkyl sulfosuccinate salt, such as dioctyl sodium sulfosuccinate; alkenyl succinate (a dipotassium salt); an alkyl phosphate salt; a naphthalene sulfonate formalin condensate; a polyoxyethylene alkyl ether sulfate salt, such as a polyoxyethylene alkylphenyl ether sulfate salt, or sodium polyoxyethylene lauryl ether sulfate; or a polyoxyethylene alkyl sulfate salt.

The cationic surfactant may be, for example, an alkyl amine salt, such as lauryl amine acetate or stearyl amine acetate; and a quaternary ammonium salt, such as lauryl trimethyl ammonium chloride. The amphoteric surfactant may be, for example, a lauryl dimethylamine oxide, a phosphate ester-based surfactant, or a phosphite ester-based surfactant. Any one of these surfactants may be used alone, or alternatively two or more of them may be used in any combination. Among the surfactants, an anionic surfactant is preferred for stability of dispersion in polymerization.

The second monomer mixture may contain a polymerization initiator when necessary. The polymerization initiator may be dispersed in an aqueous medium after being mixed with the second monomer mixture in advance. Alternatively, both the polymerization initiator and the second monomer mixture may be individually dispersed in an aqueous medium before they are mixed. Droplets of the second monomer mixture in the obtained aqueous emulsion preferably have smaller particle diameters than the seed particles so that the second monomer mixture can be efficiently absorbed by the seed particles.

The seed particles may be directly added to the aqueous emulsion. Alternatively, the seed particles may be dispersed in an aqueous medium before being added to the aqueous emulsion. After the seed particles are added to the aqueous emulsion, the seed particles are let to absorb the second monomer mixture. The absorption generally takes place by stirring the aqueous emulsion to which the seed particles have been added, at room temperature (about 20° C.) for 1 to 12 hours. The absorption may be facilitated by heating the aqueous emulsion to about 30 to 50° C.

The seed particles swell by absorbing the second monomer mixture. 100 parts by weight of the second monomer mixture is absorbed preferably by 5 to 50 parts by weight of the seed particles, and more preferably by 10 to 50 parts by weight of the seed particles. The absorption of 100 parts by weight of the second monomer mixture by less than or equal to 50 parts by weight of the seed particles enables a sufficient increase of the particle diameter during the polymerization. Productivity is thus improved. Meanwhile, the absorption of 100 parts by weight of the second monomer mixture by greater than or equal to 5 parts by weight of the seed particles facilitates the phase separation between the seed particles and the second monomer mixture, making it more likely to obtain a non-spherical shape unique to the present invention. The absorption of that amount of the second monomer mixture also prevents the second monomer mixture from being suspension-polymerized alone (without being absorbed by the seed particles) in the aqueous medium to form abnormal particles.

The second monomer mixture may be mixed with a polymerization initiator when necessary. Examples of the polymerization initiator may include organic peroxides, such as benzoyl peroxide, lauroyl peroxide, orthochlorobenzoyl peroxide, orthomethoxybenzoyl peroxide, 3,5,5-trimethylhexanoyl peroxide, t-butyl peroxy-2-ethylhexanoate, and di-t-butyl peroxide; and azo-based compounds, such as 2,2'-azobisisobutyronitrile, 1,1'-azobiscyclohexanecarbonitrile, and 2,2'-azobis(2,4-dimethyl valeronitrile). The polymerization initiator is preferably used in a range of 0.1 to 3 parts by weight to 100 parts by weight of the second monomer mixture.

In the seed polymerization step, a polymer dispersion stabilizer may be added to the aqueous emulsion to improve the stability of dispersion of obtained non-spherical resin particles. The polymer dispersion stabilizer may be, for example, a polyvinyl alcohol, a polycarboxylic acid, a cellulose (hydroxyethyl cellulose, carboxymethyl cellulose, etc.), or a polyvinylpyrrolidone. In addition, a polymer dispersion stabilizer and an inorganic water-soluble polymer compound, such as sodium tripolyphosphate, may be used together. Among these polymer dispersion stabilizers, a polyvinyl alcohol and a polyvinylpyrrolidone are preferred. The polymer dispersion stabilizer is preferably added in an amount of from 1 to 10 parts by weight to 100 parts by weight of the second monomer mixture.

In addition, in the seed polymerization step, a nitrite such as sodium nitrite, a sulfite, a hydroquinone, an ascorbate, a water-soluble vitamin B, a citrate, or a water-soluble polymerization inhibitor such as a polyphenol, may be added to the aqueous emulsion to reduce emulsion particles forming in the aqueous phase. The polymerization inhibitor is preferably added in an amount of from 0.02 to 0.2 parts by weight to 100 parts by weight of the second monomer mixture.

Next, the second monomer mixture absorbed by the seed particles is polymerized to obtain non-spherical resin particles. The polymerization temperature may be selected as appropriate according to the type of the second monomer mixture and that of the polymerization initiator. The polymerization temperature is preferably 25 to 110° C. and more preferably 50 to 100° C. The polymerization reaction is preferably carried out at elevated temperature after the seed particles have completely absorbed the second monomer mixture. After completion of the polymerization, the non-spherical resin particles are separated out from the aqueous medium by, for example, filtering, the aqueous medium may, if necessary, be removed from the non-spherical resin particles by, for example, centrifugation, and the non-spherical resin particles may, if necessary, be washed in water and a solvent before being dried.

Non-spherical resin particles are hence obtained each of which includes a concave portion (cavity) and a convex portion formed in the concave portion, wherein the convex portion has a quasi-spherical surface.

The non-spherical resin particles of the present invention may be manufactured by a manufacturing method other than the manufacturing method of the present invention detailed above. For example, the non-spherical resin particles of the present invention may possibly be manufactured by a manufacturing method according to which a monofunctional (meth)acrylate which is not a branched alkyl methacrylate and has a solubility parameter value (Hansen SP value) of less than or equal to 17.3 $(MPa)^{1/2}$ is used in place of branched alkyl methacrylate in the manufacturing method of the present invention. The monofunctional (meth)acrylate which is not a branched alkyl methacrylate and has a solubility parameter value (Hansen SP value) of less than or equal to 17.3 $(MPa)^{1/2}$ may be, for example, a $C_6$ to $C_{10}$ straight chain alkyl methacrylate: specifically, n-hexyl methacrylate (Hansen SP value=17.23 $(MPa)^{1/2}$), n-heptyl methacrylate (Hansen SP value=17.03 $(MPa)^{1/2}$), n-octyl methacrylate (Hansen SP value=16.90 $(MPa)^{1/2}$), n-nonyl methacrylate (Hansen SP value=16.92 $(MPa)^{1/2}$), or n-decyl methacrylate (Hansen SP value=17.14 $(MPa)^{1/2}$).

External Preparation

The non-spherical resin particles of the present invention may be used as an ingredient for an external preparation, for example, as a slip enhancement agent for an external preparation. The external preparation of the present invention contains the non-spherical resin particles of the present invention. The non-spherical resin particles may be present in the external preparation preferably in an amount of from 1 to 80 wt % and more preferably in an amount of from 5 to 70 wt %. The non-spherical resin particle content may be determined in a suitable manner according to the type of the external preparation. If the non-spherical resin particle content is less than 1 wt % to the whole external preparation, the non-spherical resin particles may fail to produce an appreciable effect. On the other hand, if the non-spherical resin particle content is in excess of 80 wt %, the resultant effect might be smaller than could be expected for the extra content. This is not desirable in terms of production cost.

Examples of the external preparation may include cosmetics and external medicines.

The cosmetics are by no means limited in any particular manner as long as they produce an effect when they contain the non-spherical resin particles. Examples of the cosmetics may include liquid-based cosmetics, such as pre-shave lotions, body lotions, skin lotions, cosmetic creams, milky lotions, body shampoos, and antiperspirants; cleansing cosmetics, such as soaps and scrub cleansers; facial packs; shaving creams; face powders; makeup foundations; lipsticks; lip balms; cheek color; eye makeup cosmetics; nail polish cosmetics; hair washing cosmetics; hair coloring preparations; hair dressings; aromatic cosmetics; toothpastes; bath preparations; sunscreen products; suntan products; and body cosmetics, such as body powders and baby powders.

The external medicines are by no means limited in any particular manner as long as they are applicable to skin. Examples may include medical creams, ointments, medical emulsions, and medical lotions.

These external preparations may be blended with a commonly used base agent or additive suitable for an intended purpose as long as the effect of the invention is maintained. Examples of the base agent or additive may include water, lower alcohols (alcohols with 5 or less carbon atoms), oils and waxes, hydrocarbons (vaseline, liquid paraffins, etc.), higher fatty acids (stearin acid and like fatty acids with 12 or more carbon atoms), higher alcohols (cetyl alcohol and like alcohols with 6 or more carbon atoms), sterols, fatty acid esters (octyldodecyl myristates, oleates, etc.), metal soaps, moisturizing agents, surfactants (polyethylene glycols, etc.), polymer compounds, clay minerals (multifunctional components serving as extender pigments, adsorbents, etc.; talc and mica), ingredients for coloring agents (red iron oxide, yellow iron oxide, etc.), perfumes, antiseptics/disinfectants, antioxidants, ultraviolet absorbers, resin particles, such as acrylic resin particles (poly(meth)acrylate particles), silicone-based particles, and polystyrene particles, non-spherical resin particles which are not the non-spherical resin particles of the present invention, pH adjusters (e.g., triethanol amine), special blend additives, and medical active ingredients.

Coating Material

The non-spherical resin particles of the present invention may be present in coating materials as, for example, a coat softener or a coating material flatting agent. The coating material containing the non-spherical resin particles of the present invention may, when necessary, contain at least one of a binder resin and a solvent. The binder resin used may be a resin soluble in an organic solvent or water or an aqueous, emulsion-type resin dispersible in water. The binder resin may be, for example, an acrylic resin, an alkyd resin, a polyester resin, a polyurethane resin, a chlorinated polyolefin resin, or an amorphous polyolefin resin. Any appropriate one of these binder resins may be selected according to the adhesion of the coating material to the base material to be coated and the environment in which the coating material is to be used.

The amounts of the binder resin and non-spherical resin particles being added vary also with the thickness of the produced coat, the average particle diameter of the non-spherical resin particles, and a coating method. The binder resin is added preferably in an amount of from 5 to 50 wt %, more preferably in an amount of from 10 to 50 wt %, and even more preferably in an amount of from 20 to 40 wt %, to the combined, amount of the binder resin (the solid content in the case of an aqueous, emulsion-type resin being used) and the non-spherical resin particles.

The non-spherical resin particles are added preferably in an amount of from 5 to 50 wt %, more preferably in an amount of from 10 to 50 wt %, and even more preferably in an amount of from 20 to 40 wt %, to the combined amount of the binder resin (the solid content in the case of an aqueous, emulsion-type resin being used) and the non-spherical resin particles. If the non-spherical resin particle content is less than 5 wt %, a sufficient matting effect may not be achieved. On the other hand, if the non-spherical resin particle content is in excess of 50 wt %, the coating material composition may be so viscous that the non-spherical resin particles cannot disperse sufficiently. That might in turn lead to a poor appearance of the coat, including micro cracks developing in the obtained coat and a rough texture of the surface of the obtained coat.

The solvent used as a component of the coating material, although not limited in any particular manner, is preferably a solvent capable of dissolving or dispersing the binder resin. For example, when the coating material is an oil-based coating material, the solvent may be, for example, a hydrocarbon-based solvent, such as toluene or xylene; a ketone-based solvent, such as methyl ethyl ketone or methyl isobutyl ketone; an ester-based solvent, such as ethyl acetate or butyl acetate; or an ether-based solvent, such as dioxane, ethylene glycol diethyl ether, or ethylene glycol monobutyl ether. When the coating material is an aqueous coating material, the solvent may be, for example, water or an alcohol. Any one of these solvents may be used alone, or alternatively two or more of them may be mixed for use. The solvent content of the coating material is typically from 20 to 60 wt % to the total amount of the coating material.

The coating material may, when necessary, contain a publicly known coat surface adjuster, fluidity adjuster, ultraviolet absorber, light stabilizer, curing catalyst, filler, coloring pigment, metal pigment, mica powder pigment, or dye.

When a coating material is to be used, the method of forming a coat is by no means limited in any particular manner and may be any publicly known method. The method of forming a coat may be, for example, spray coating, roll coating, or brush coating. The coating material, when necessary, may be diluted by adding a diluent to it, to adjust its viscosity. The diluent may be, for example, a hydrocarbon-based solvent, such as toluene or xylene; a ketone-based solvent, such as methyl ethyl ketone or methyl isobutyl ketone; an ester-based solvent, such as ethyl acetate or butyl acetate; an ether-based solvent, such as dioxane or ethylene glycol diethyl ether; water; or an alcohol-based solvent. Any one of these diluents may be used alone, or alternatively two or more of them may be mixed for use.

Light Diffusing Resin Composition

The non-spherical resin particles of the present invention may be used as a light diffusing resin composition if the particles are dispersed in a transparent base resin (transparent resin) as a light diffusing agent. In other words, the light diffusing resin composition may contain the non-spherical resin particles of the present invention and a transparent base resin. The light diffusing resin composition may be used as an ingredient for a light diffusion member such as a light cover (e.g., a light cover for light-emitting diode (LED) illumination or a light cover for fluorescent tube illumination), a light diffusion sheet or film, and a light diffusion plate.

The transparent base resin used is typically a thermoplastic resin different from the resin composing the non-spherical resin particles. The thermoplastic resin used as the transparent base resin may be, for example, an acrylic resin, a (meth)acrylate/styrene copolymer, a polycarbonate, a polyester, a polyethylene, a polypropylene, or a polystyrene. Among these thermoplastic resins, acrylic resins, (meth)acrylate/styrene copolymers, polycarbonates, polyesters, and polystyrenes are preferred when the transparent base resin is required to provide excellent transparency. Any one of these thermoplastic resins may be used alone, or alternatively two or more of them may be used in any combination.

The non-spherical resin particles are added to the transparent base resin preferably in an amount of from 0.01 to 40 parts by weight, more preferably in an amount of from 0.1 to 10 parts by weight, to 100 parts by weight of the transparent base resin. If the non-spherical resin particles are less than 0.01 parts by weight, the obtained light diffusion member may not deliver sufficient light diffusion. If the non-spherical resin particles are more than 40 parts by weight, the obtained light diffusion member, despite being capable of delivering sufficient light diffusion, may have a low optical transparency.

The manufacturing method for the light diffusing resin composition is by no means limited in any particular manner. The light diffusing resin composition may be manufactured by mixing non-spherical resin particles and a transparent base resin by a publicly known, conventional method, for example, mechanical pulverization and mixing. According to mechanical pulverization and mixing, the light diffusing resin composition may be manufactured by mixing and stirring non-spherical resin particles and a transparent base resin using, for example, a Henschel mixer, a V-shaped mixer, a Turbula mixer, a hybridizer, a rocking mixer, or like apparatus.

The light diffusing resin composition may be molded into a light cover, a light diffusion sheet, or another light diffusion member in accordance with the present invention. When this is the case, for example, a light diffusing agent and a transparent base resin are mixed in a mixer and kneaded in an extruder or a like melting kneading machine to form pellets of the light diffusing resin composition. The pellets are then either molded by extrusion or melted and molded by injection, to obtain a light diffusion member of any shape.

The light diffusion sheet may be used, for example, as a light diffusion sheet for a liquid crystal display device. The structure of the liquid crystal display device is not limited in any particular manner as long as the liquid crystal display device can contain a light diffusion sheet. For example, the liquid crystal display device may include at least a liquid crystal display panel with a display surface and a backside, a light guide plate disposed in the backside of the liquid crystal display panel, and a light source emitting light incident to a side face of the light guide plate. The liquid crystal display device may further include a light diffusion sheet on a face of the light guide plate facing the liquid crystal display panel and a reflection sheet on a face of the light guide plate opposite that face. This light source arrangement is referred to generally as an edge-light backlight arrangement. An alternative light source arrangement to the edge-light backlight arrangement is a direct backlight arrangement in which, specifically, a light source is disposed in the backside of the liquid crystal display panel with at least a light diffusion sheet located between the liquid crystal display panel and the light source.

Light Diffusing Coating Age

The coating material containing the non-spherical resin particles may be used as a light diffusing coating agent, for example, for paper or a light diffusion member, if the coating material is transparent and contains a binder resin, in other words, if the coating material contains a transparent binder resin, but does not contain pigment, dye, or any other non-transparent material. When this is the case, the non-spherical resin particles act as a light diffusing agent.

The light diffusion member of the present invention may be manufactured by coating a transparent base material as a base material with a light diffusing coating agent (light diffusion member coating agent) to form a transparent coat (light diffusing coating).

An appropriate transparent base material may, for example, be selected for use from resin base materials made of a resin, such as polyethylene terephthalate (PET), polyester, acrylic resin, polycarbonate, or polyamide, and inorganic base materials such as a transparent glass sheet. The thickness of the transparent base material, although not limited in any particular manner, is preferably in the range of 10 to 500 μm for ease in fabrication and handling.

Any publicly known method, such as reverse roll coating, gravure coating, die coating, comma coating, or spray coating, may be used to form a light diffusing coating. A preferred method is such that roughness originating from the non-spherical resin particles can be formed on the surface of a coat.

The thickness of the light diffusing coating, although not limited in any particular manner, is preferably in the range of 1 to 100 μm and more preferably in the range of 3 to 30 μm, taking light diffusing, strength, and other conditions into consideration.

A light diffusion member obtained by coating with a light diffusion member coating agent may be used as an anti-glare film. Alternatively, the light diffusion member may be used for the same uses as the light diffusion member obtained by molding the light diffusing resin composition mentioned above.

The light diffusing coating agent (paper coating agent) may be applied to paper as a base material, hence forming a transparent coat, to manufacture matte paper. Any of the methods mentioned above may be used to apply the light diffusing coating agent. A preferred method is such that roughness originating from the non-spherical resin particles can be formed on the surface of the coat.

EXAMPLES

The following will describe the present invention by means of examples and comparative examples. The present invention is however by no means limited to them.

Method of Measuring Average Particle Diameter of Seed Particles

The average particle diameter of seed particles was measured by a laser diffraction particle size analyzer (LS230 manufactured by Beckman Coulter, Inc.). Specifically, seed particles (0.1 g) and a 0.1% nonionic surfactant solution (10 ml) were introduced into a test tube and mixed for 2 seconds in a touch mixer (Touch Mixer MT-31 manufactured by Yamato Scientific Co., Ltd.). Thereafter, the content of the test tube was dispersed for 10 minutes using a commercially available ultrasonic cleaner (Ultrasonic Cleaner VS-150 manufactured by Velvo-clear Co., Ltd.) to obtain a dispersion liquid. With the dispersion liquid being placed under ultrasonic irradiation, the average particle diameter of the seed particles in the dispersion liquid was measured by a laser diffraction particle size analyzer (LS230 manufactured by Beckman Coulter, Inc.). The optical model used for that purpose was adjusted to the refractive index of the particles produced.

Method of Measuring Average Particle Diameter of Non-Spherical Resin Particles

The average particle diameter of the non-spherical resin particles was measured by the Coulter Principle using a Coulter counter analyzer Multisizer II (manufactured by Beckman Coulter, Inc.). The Multisizer II was calibrated using a 50-μm aperture according to the "Reference Manual for the Coulter Multisizer (1987)" published by Coulter Electronics Limited before measurement of the average particle diameter was carried out.

Specifically, non-spherical resin particles (0.1 g) were dispersed in a 0.1% aqueous, nonionic surfactant solution (10 ml) under ultrasonic irradiation using a touch mixer, to obtain a dispersion liquid. While gently stirring, the dispersion liquid was dispensed dropwise using a dropper into a beaker, which is filled with a measurement electrolyte solution "ISOTON® II" (manufactured by Beckman Coulter, Inc.), attached to the main body of the Multisizer II. The density meter on the screen of the main body of the Multisizer II was adjusted to yield readings of about 10%. Next, an aperture size (diameter) of 50 μm, a current (aperture current) of 800 μA, a gain of 4, and a positive polarity (of the inner electrode) were entered on the main body of the Multisizer, and a volume-based particle size distribution was measured manually (in manual mode). For the aperture size, etc., different values may be entered as needed. The content of the beaker was stirred so gently during measurement that no bubbles could form. The measurement was terminated when the particle size distribution of 100,000 particles was measured. An arithmetic average diameter was obtained from the volume-based particle size distribution and taken as the average particle diameter.

Method of Measuring Coefficient of Variation (CV Value) of Particle Diameters of Non-Spherical Resin Particles The CV value of the particle diameters of the non-spherical resin particles was calculated by the following equation, using the standard deviation (σ) and the average particle diameter (D) obtained from the volume-based particle size distribution measurement.

$$CV \text{ value}(\%) = (\sigma/D) \times 100$$

Seed Particle Preparation Example 1

First, pure water (3,500 g) as an aqueous medium was put in a reaction vessel equipped with a stirrer and a thermometer. Next, methyl methacrylate (396 g) and n-octyl mercaptan (1.2 g) as a chain transfer agent were introduced to the pure water in the reaction vessel. Subsequently, the content was subjected to nitrogen purge (nitrogen substitution) and heated to 55° C. Thereafter, a solution in which potassium persulfate (2.0 g) as a polymerization initiator had been dissolved in pure water (100 g) was added to the content of the reaction vessel. The whole content was then subjected to another round of nitrogen purge, followed by polymerization at 55° C. for 12 hours while stirring, to obtain seed particles ("seed particles (1)") in slurry form. The average particle diameter of seed particles (1) was measured by the aforementioned method to be 0.45 μm.

Seed Particle Preparation Example 2

First, pure water (3,500 g) as an aqueous medium was put in a reaction vessel equipped with a stirrer and a thermometer. Next, methyl methacrylate (396 g), ethylene glycol dimethacrylate (4 g) as a polyfunctional monomer, n-octyl mercaptan (1.2 g) as a chain transfer agent, and seed particles (1) (285 g) obtained in seed particle preparation example 1 as a (meth)acrylate polymer were introduced to the pure water in the reaction vessel. Subsequently, the content of the reaction vessel was subjected to nitrogen purge and heated to 55° C. Thereafter, a solution in which potassium persulfate (2.0 g) as a polymerization initiator had been dissolved in pure water (100 g) was added to the content of the reaction vessel. The whole content was then subjected to another round of nitrogen purge, followed by polymerization at 55° C. for 12 hours while stirring, to obtain seed particles ("seed particles (2)") in slurry form. The average particle diameter of seed particles (2) was measured by the aforementioned method to be 1.0 μm.

Seed Particle Preparation Example 3

Seed particles were prepared in the same manner as in seed particle preparation example 2, except that isobutyl methacrylate (396 g), instead of methyl methacrylate, was used as a branched alkyl methacrylate. Seed particles were hence obtained in slurry form ("seed particles (3)"). The average particle diameter of seed particles (3) was measured by the aforementioned method to be 1.0 μm.

Seed Particle Preparation Example 4

Seed particles were prepared in the same manner as in seed particle preparation example 2, except that the amount of the n-octyl mercaptan was changed from 1.2 g to 4 g. Seed particles were hence obtained in slurry form ("seed particles (4)"). The average particle diameter of seed particles (4) was measured by the aforementioned method to be 1.0 μm.

Seed Particle Preparation Example 5

Seed particles were prepared in the same manner as in seed particle preparation example 2, except that isobutyl methacrylate (398 g), instead of methyl methacrylate, was used as a branched alkyl methacrylate and that the amount of the ethylene glycol dimethacrylate was changed from 4 g to 2 g. Seed particles were hence obtained in slurry form ("seed particles (5)"). The average particle diameter of seed particles (5) was measured by the aforementioned method to be 1.0 μm.

Seed Particle Preparation Example 6

First, ion exchanged water (200 parts by weight) and isopropyl alcohol (5 parts by weight), as an aqueous medium, were put in a reaction vessel equipped with a stirrer and a thermometer. Next, methyl trimethoxy silane (25 parts by weight, trade name: KBM-13, manufactured by Shin-Etsu Chemical Co., Ltd.) and 3-methacryloxypropyl trimethoxy silane (5 parts by weight, trade name: KBM-503, manufactured by Shin-Etsu Chemical Co., Ltd.) were added. The whole content was stirred continuously for 2 hours and cooled to 25° C. While stirring, 0.5% ammonia water (5 parts by weight) was added, and the whole content was stirred for 1 minute. Stirring was then stopped, and the mixture was let to stand for 4 hours to obtain seed particles ("seed particles (6)"). The average particle diameter of seed particles (6) was measured by the aforementioned method to be 2.70 μm.

Seed Particle Preparation Example 7

Methyl methacrylate (66.7 parts by weight), ethylene glycol dimethacrylate (0.0078 parts by weight), benzoyl peroxide (1.0 parts by weight), sodium dodecylbenzenesulfonate (0.5 parts by weight), sodium nitrate (0.1 parts by weight), and ion exchanged water (200 parts by weight) were stirred at 10,000 rpm for 3 minutes by using a homogenizer mixer.

The mixture was transferred to a 1-liter, four-neck flask equipped with a thermometer and a nitrogen gas introduction tube. Seed particles (6) (33.3 parts by weight) and ion exchanged water (40 parts by weight) were then added to the mixture, and the whole content was gently stirred at 50° C. for 30 minutes.

Thereafter, a 5% aqueous PVA solution (40 parts by weight) was added. The content was reacted at 75° C. for 1 hour and at 90° C. for another hour to obtain seed particles (7). The average particle diameter of seed particles (7) was measured by the aforementioned method to be 3.89 μm. Seed particles (7) were spherical monodisperse particles.

Example 1

Seed Polymerization

First, ion exchanged water (80 g) as an aqueous medium was put in a reaction vessel equipped with a high speed stirrer and a thermometer. Next, dioctyl sodium sulfosuccinate (0.8 g, trade name: RAPISOL® A-80 manufactured by NOF Corporation) as a anionic surfactant was added to the ion exchanged water in the reaction vessel. Thereafter, butyl methacrylate (56 g) as a monofunctional aliphatic monomer, ethylene glycol dimethacrylate (24 g) as a polyfunctional monomer, and benzoyl peroxide (0.5 g) as a polymerization initiator were added to the content of the reaction vessel. The whole content was then stirred at 8000 rpm for 10 minutes in a high speed stirrer to obtain a emulsion.

Thereafter, 36.6 g of seed particles (3) obtained in seed particle preparation example 3 was added to the emulsion so that seed particles (3) could swell by absorbing the emulsion over 2 hours at 30° C. Then, ion exchanged water (240 g) as an aqueous medium and polyvinyl alcohol (3.2 g) as a polymer dispersion stabilizer were added to the content of the reaction vessel. Sodium nitrite (0.064 g) was also added as a polymerization inhibitor, and the whole content was polymerized at 50° C. for 6 hours while stirring. The polymerized reaction liquid was filtered to separate out resin particles from the reaction liquid. The separated resin particles were well washed in warm water and dried to obtain resin particles.

Figure 3:
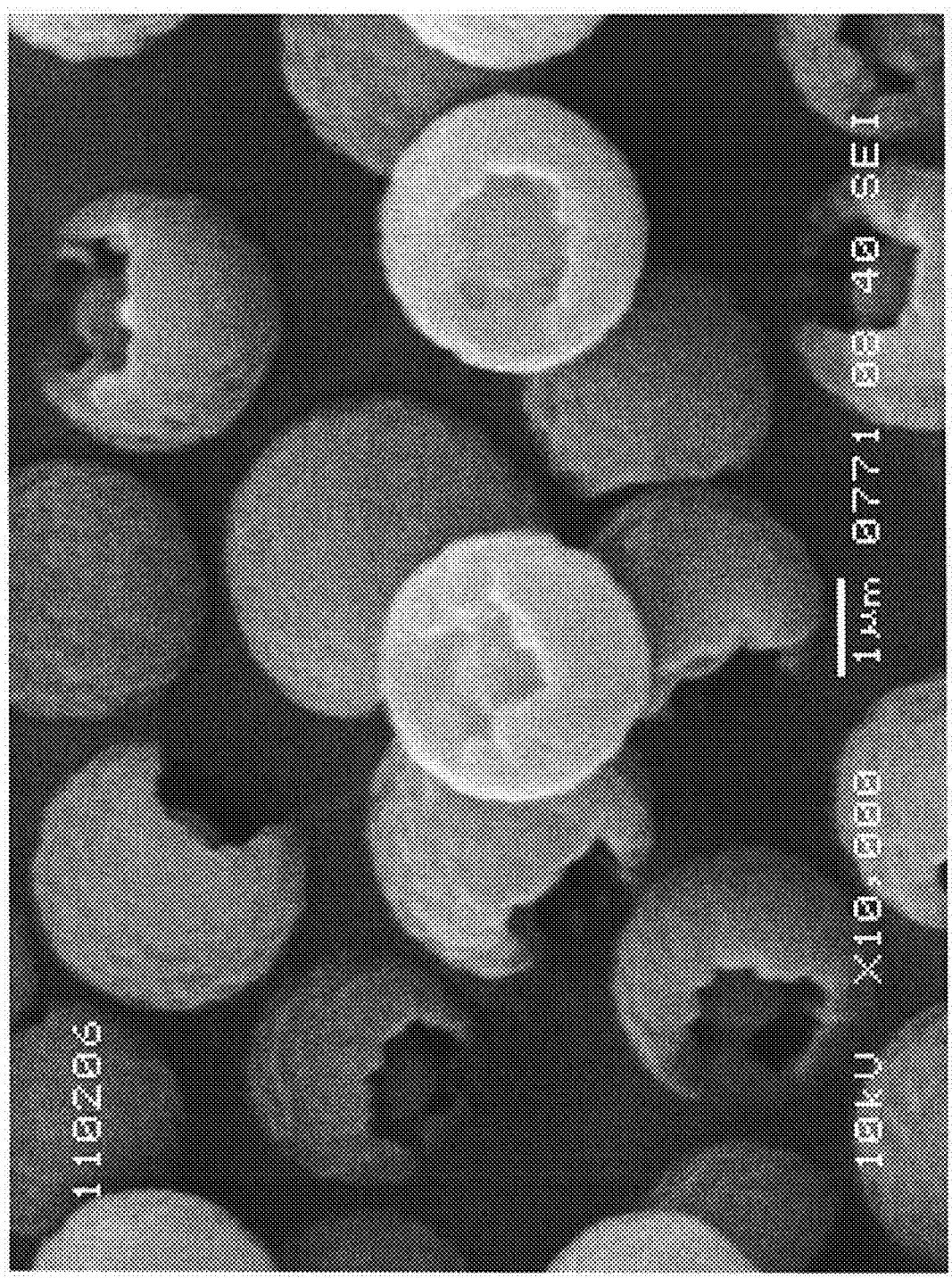
FIG. 3 is an image obtained from scanning electron microscope (SEM) imaging of the surface of a non-spherical resin particle obtained in example 1 of the present invention.

The obtained resin particles were imaged under a scanning electron microscope (SEM). An obtained resin particle was sliced to take out a thin piece thereof containing the center of the resin particle. The thin piece was stained and imaged under a transmission electron microscope (TEM). These results show, as can be seen in the SEM image of FIG. 3 and the TEM image of FIG. 4, that the resin particles were non-spherical resin particles having such a shape that a portion of the quasi-sphere was missing to form a concave portion therein, and a convex portion with a quasi-spherical surface was formed in the concave portion. The SEM image of FIG. 3 also shows that roughness smaller than the convex and concave portions was formed (second concave portions smaller than the concave portion were formed) on the surface of a non-concave portion of the non-spherical resin particles (the surface of the quasi-spherical shell).

Figure 4:
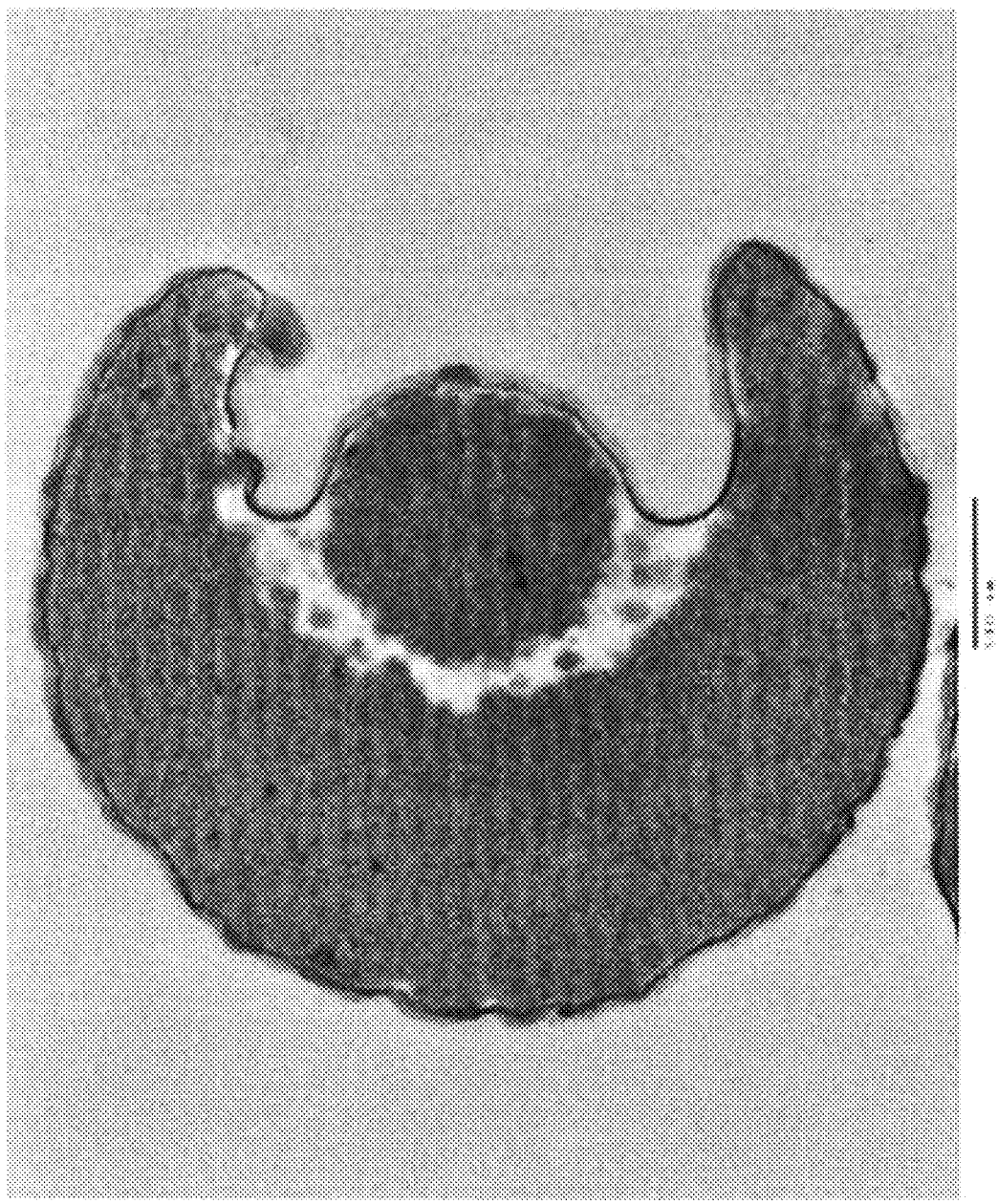
FIG. 4 is an image obtained from transmission electron microscope (TEM) imaging of a cross-section of a non-spherical resin particle obtained in example 1 of the present invention.

From the TEM image of FIG. 4 (the scale bar visible at the bottom indicates a length of 500 nm) were measured a maximum diameter "a" of the non-spherical resin particle, a diameter "b" of the convex portion (the distance from the deepest point in the upper concave portion to the deepest point in the lower concave portion in the cross-section shown in FIG. 4), and a diameter "c" of the concave portion (the distance from the tip of the convex portion near the top of the cross-section shown in FIG. 4 to the tip of the convex portion near the bottom thereof). The dimension ratios b/a and c/a were calculated to be 0.36 and 0.50 respectively.

The average particle diameter of the obtained non-spherical resin particles was measured by the aforementioned method to be 2.5 µm. The CV value of the particle diameters of the obtained non-spherical resin particles was measured by the aforementioned method to be 12%, which indicates that the non-spherical resin particles were monodisperse particles.

Example 2

Resin particles were prepared by the same manufacturing method as in example 1, except that isobutyl methacrylate (56 g), instead of butyl methacrylate (56 g), was used as a monofunctional aliphatic monomer.

Figure 5:
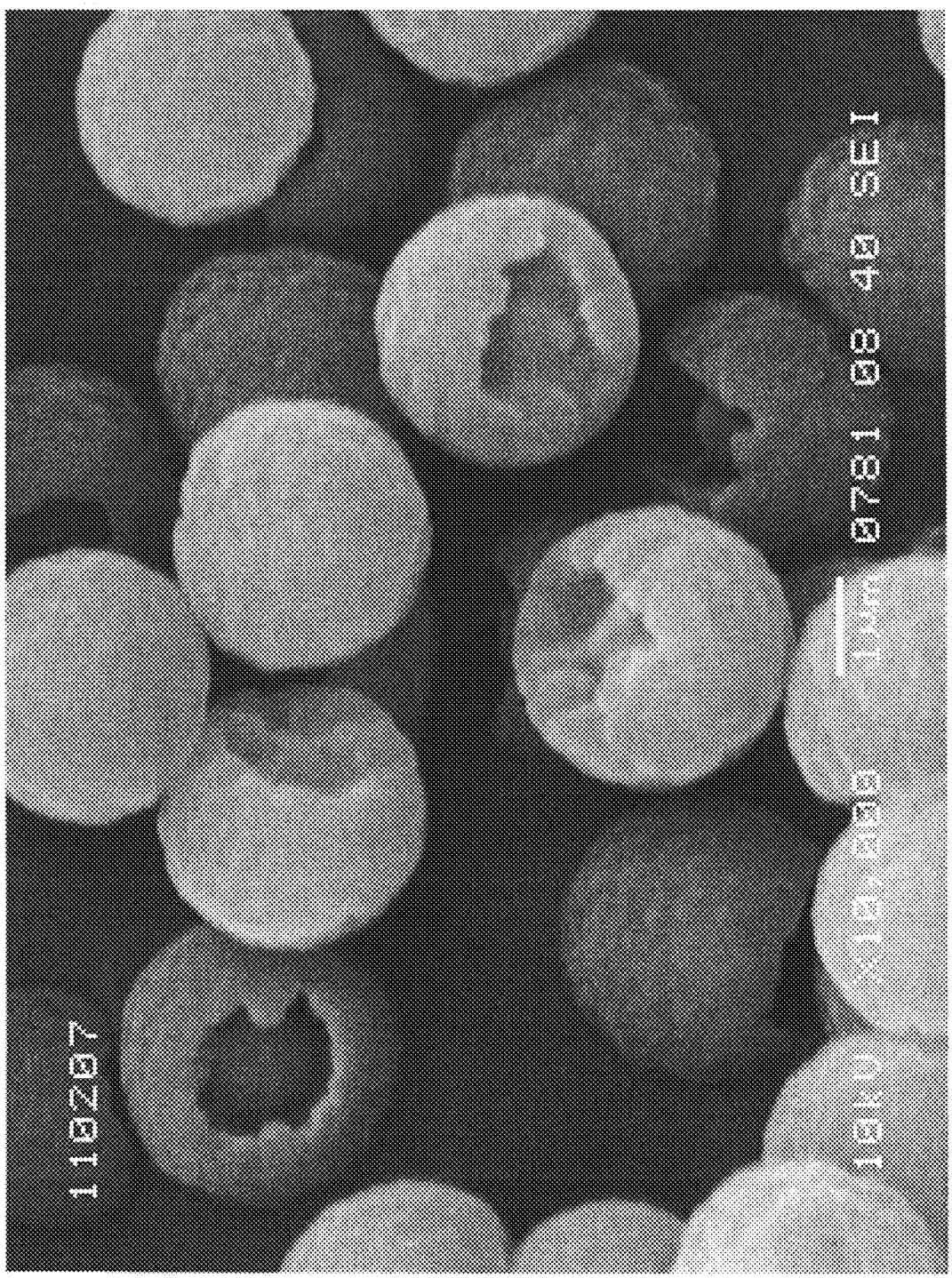
FIG. 5 is an image obtained from SEM imaging of the surface of a non-spherical resin particle obtained in example 2 of the present invention.

The obtained resin particles were imaged under an SEM. An obtained resin particle was sliced to take out a thin piece thereof containing the center of the resin particle. The thin piece was stained and imaged under a TEM. These results show, as can be seen in the SEM image of FIG. 5 and the TEM image of FIG. 6, that the resin particles were non-spherical resin particles having such a shape that a portion of the quasi-sphere was missing to form a concave portion therein, and a convex portion with a quasi-spherical surface was formed in the concave portion. The SEM image of FIG. 5 also shows that roughness smaller than the convex and concave portions was formed (second concave portions smaller than the concave portion were formed) on the surface of a non-concave portion of the non-spherical resin particles (the surface of the quasi-spherical shell).

Figure 6:
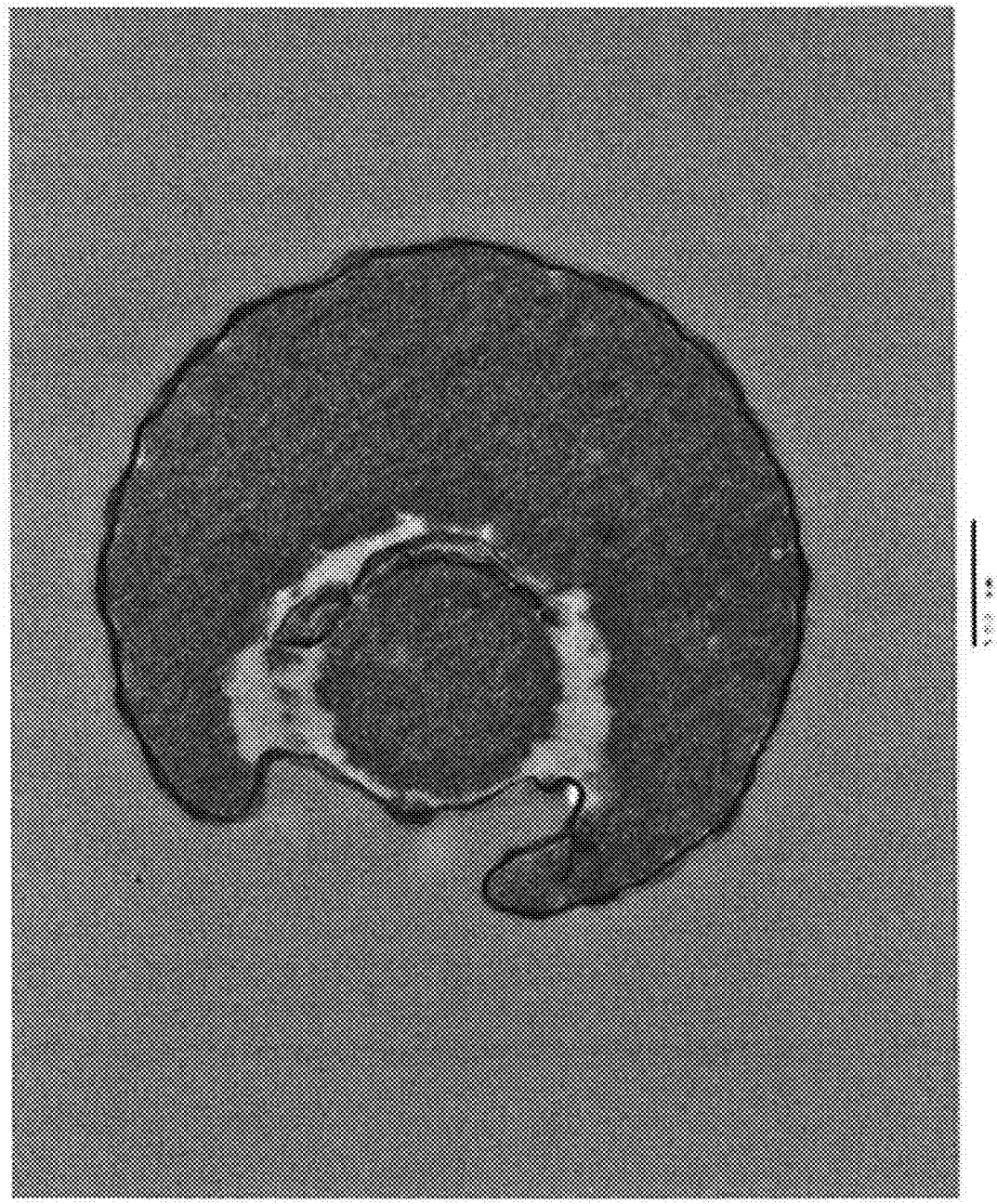
FIG. 6 is an image obtained from TEM imaging of a cross-section of a non-spherical resin particle obtained in example 2 of the present invention.

From the TEM image of FIG. 6 (the scale bar visible at the bottom indicates a length of 500 nm) were measured a maximum diameter "a" of the non-spherical resin particle, a diameter "b" of the convex portion, and a diameter "c" of the concave portion. The dimension ratios b/a and c/a were calculated to be 0.30 and 0.35 respectively.

The average particle diameter of the obtained non-spherical resin particles was measured by the aforementioned method to be 2.5 µm. The CV value of the particle diameters of the obtained non-spherical resin particles was measured by the aforementioned method to be 12%, which indicates that the non-spherical resin particles were monodisperse particles.

Example 3

Resin particles were prepared by the same manufacturing method as in example 1, except that methyl methacrylate (56 g), instead of butyl methacrylate (56 g), was used as a monofunctional aliphatic monomer.

Figure 7:
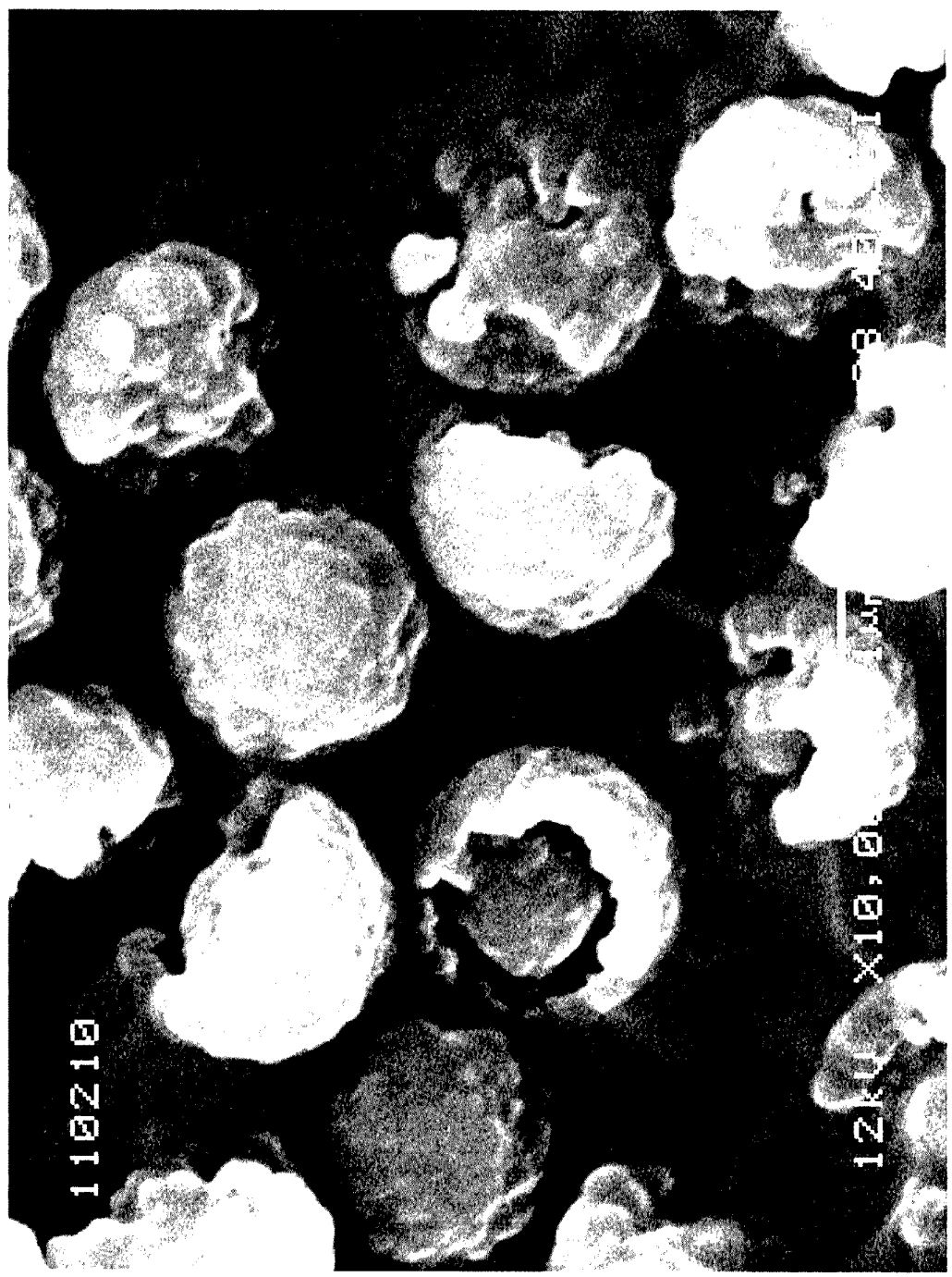
FIG. 7 is an image obtained from SEM imaging of the surface of a non-spherical resin particle obtained in example 3 of the present invention.

The obtained resin particles were imaged under an SEM. An obtained resin particle was sliced to take out a thin piece thereof containing the center of the resin particle. The thin piece was stained and imaged under a TEM. These results show, as can be seen in the SEM image of FIG. 7 and the TEM image of FIG. 8, that the resin particles were non-spherical resin particles having such a shape that a portion of the quasi-sphere was missing to form a concave portion therein, and a convex portion with a quasi-spherical surface was formed in the concave portion. The SEM image of FIG. 7 also shows that roughness smaller than the convex and concave portions, but larger than the roughness on the surface of the non-spherical resin particles of examples 1 and 2 was formed (second concave portions smaller than the concave portion, but larger than the second concave portions on the surface of the shell of the non-spherical resin particles of examples 1 and 2 were formed) on the surface of a non-concave portion of the non-spherical resin particles (the surface of the quasi-spherical shell).

Figure 8:
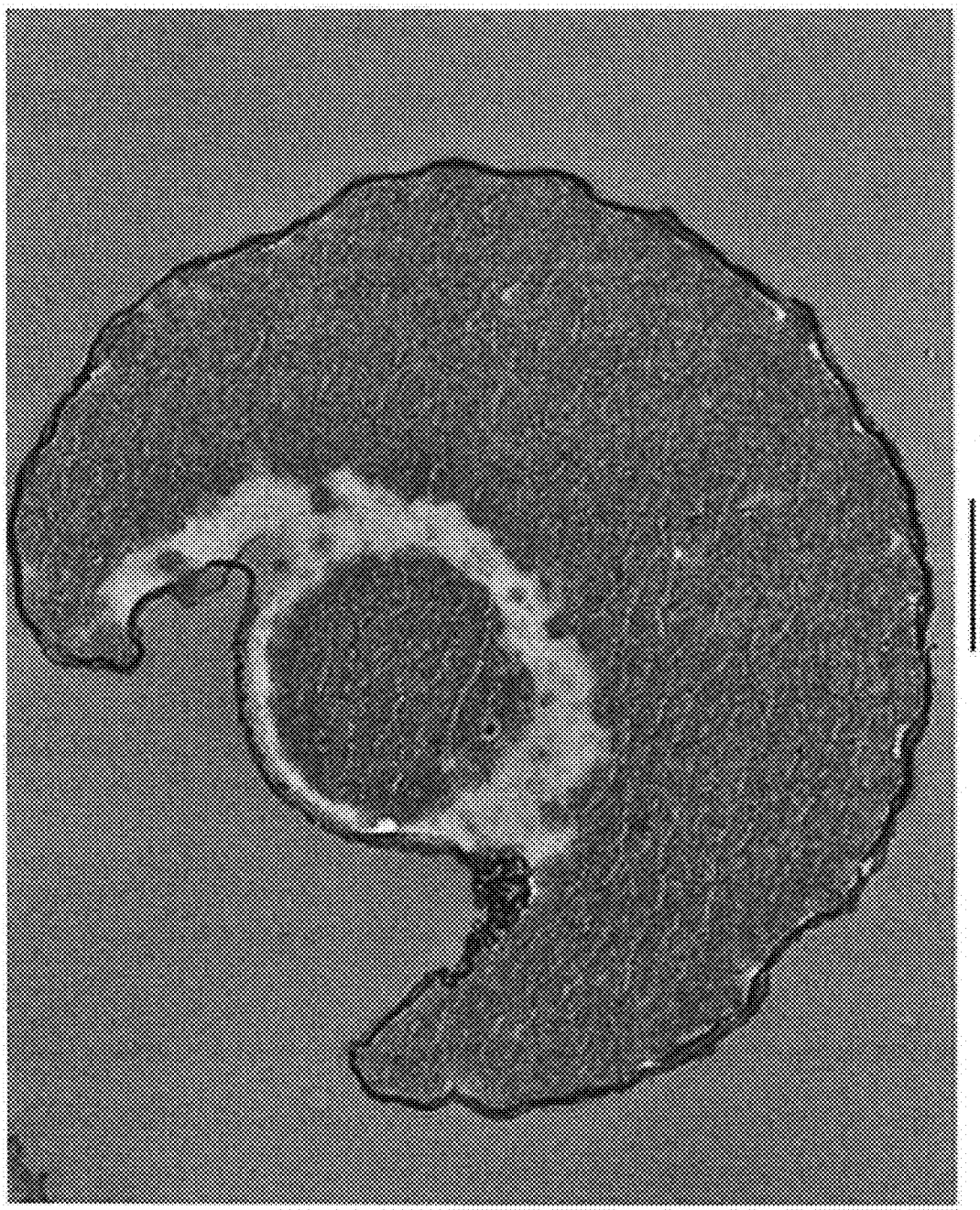
FIG. 8 is an image obtained from TEM imaging of a cross-section of a non-spherical resin particle obtained in example 3 of the present invention.

From the TEM image of FIG. 8 (the scale bar visible at the bottom indicates a length of 500 nm) were measured a maximum diameter "a" of the non-spherical resin particle, a diameter "b" of the convex portion, and a diameter "c" of the concave portion. The dimension ratios b/a and c/a were calculated to be 0.51 and 0.50 respectively.

The average particle diameter of the obtained non-spherical resin particles was measured by the aforementioned method to be 2.5 µm. The CV value of the particle diameters of the obtained non-spherical resin particles was measured by the aforementioned method to be 10%, which indicates that the non-spherical resin particles were monodisperse particles.

Example 4

Resin particles were prepared by the same manufacturing method as in example 1, except that butyl methacrylate (28 g) and butyl acrylate (28 g), instead of butyl methacrylate 56 g, were used as monofunctional aliphatic monomers.

Figure 9:
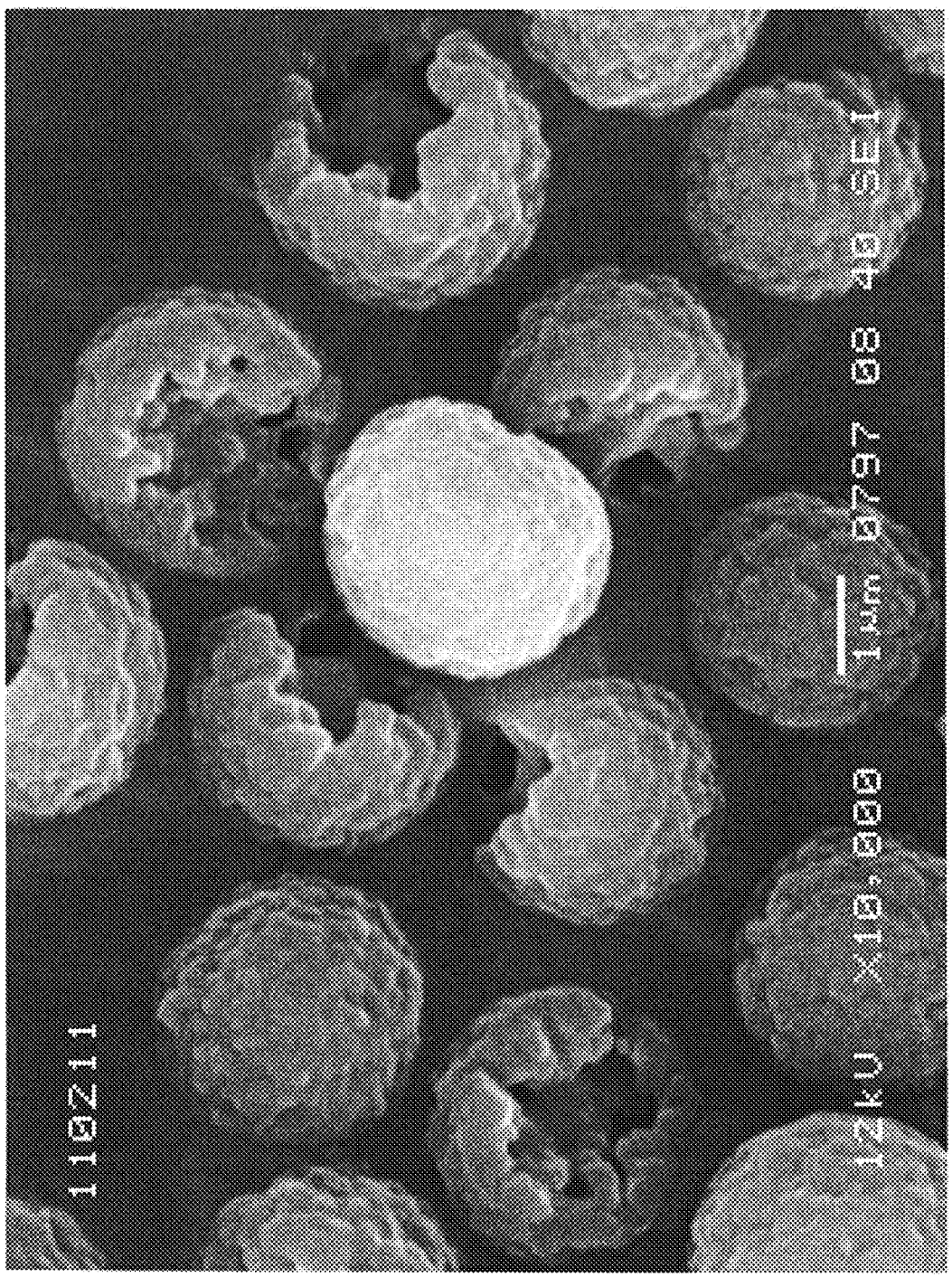
FIG. 9 is an image obtained from SEM imaging of the surface of a non-spherical resin particle obtained in example 4 of the present invention.

The obtained resin particles were imaged under an SEM. An obtained resin particle was sliced to take out a thin piece thereof containing the center of the resin particle. The thin piece was stained and imaged under a TEM. These results show, as can be seen in the SEM image of FIG. 9 and the TEM image of FIG. 10, that the resin particles were non-spherical resin particles having such a shape that a portion of the quasi-sphere was missing to form a concave portion therein, and a convex portion with a quasi-spherical surface was formed in the concave portion. The SEM image of FIG. 9 also shows that roughness smaller than the convex and concave portions, but larger than the roughness on the surface of the non-spherical resin particles of examples 1 and 2 was formed (second concave portions smaller than the concave portion, but larger than the second concave portions on the surface of the shell of the non-spherical resin particles of examples 1 and 2 were formed) on the surface of a non-concave portion of the non-spherical resin particles (the surface of the quasi-spherical shell).

Figure 10:
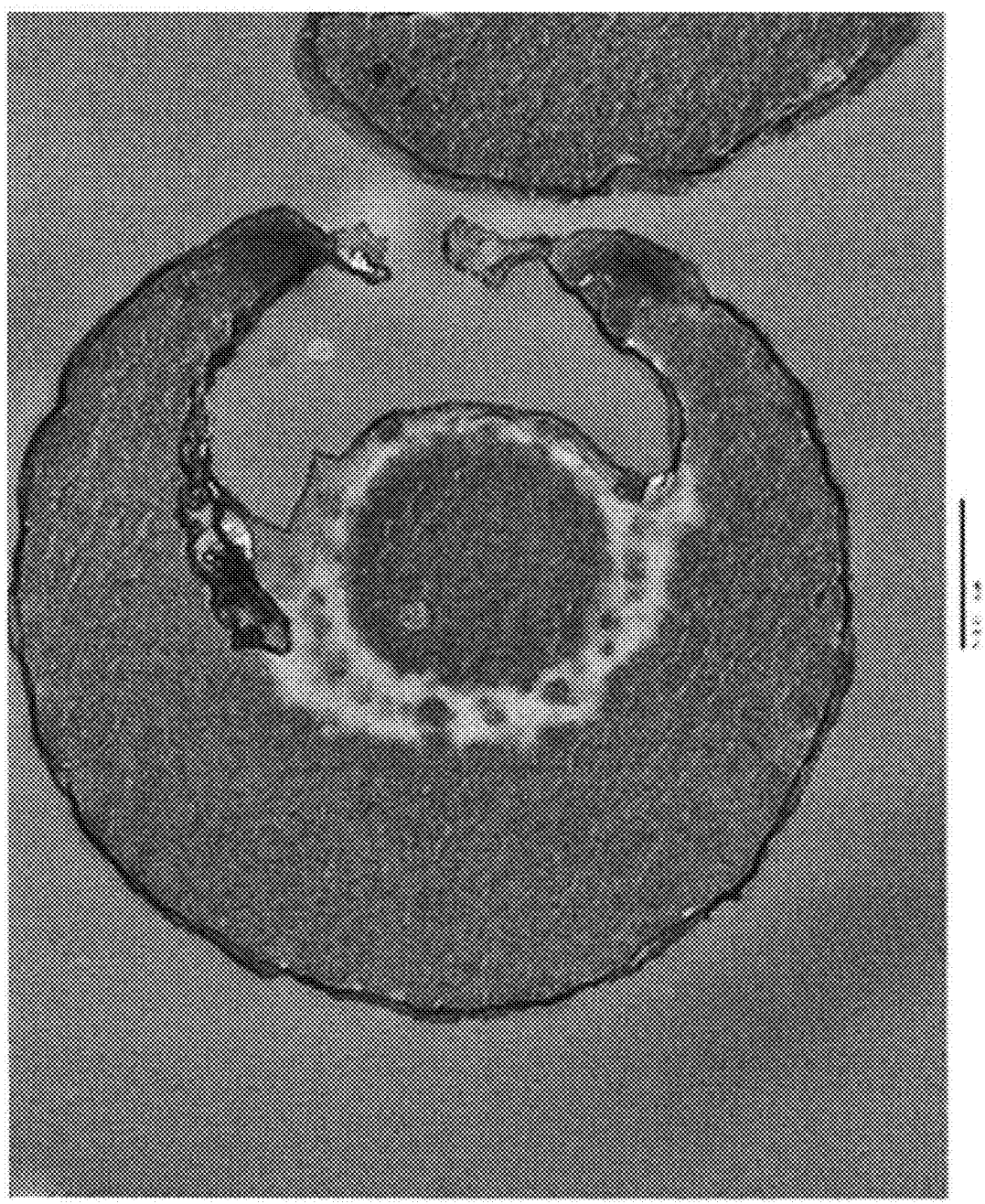
FIG. 10 is an image obtained from TEM imaging of a cross-section of a non-spherical resin particle obtained in example 4 of the present invention.

From the TEM image of FIG. 10 (the scale bar visible at the bottom indicates a length of 500 nm) were measured a maximum diameter "a" of the non-spherical resin particle, a diameter "b" of the convex portion, and a diameter "c" of the concave portion. The dimension ratios b/a and c/a were calculated to be 0.43 and 0.26 respectively.

The average particle diameter of the non-spherical resin particles obtained in example 4 was measured by the aforementioned method to be 2.5 μm. The CV value of the particle diameters of the non-spherical resin particles obtained in example 4 was measured by the aforementioned method to be 11%, which indicates that the non-spherical resin particles were monodisperse particles.

Example 5

Resin particles were prepared by the same manufacturing method as in example 1, except that poly(ethylene glycol-propylene glycol) monomethacrylate (8.0 g, product name: Blemmer® 50 PEP-300, manufactured by NOF Corporation; in the formula (I), $R_1=CH_3$, $R_2=C_2H_4$, $R_3=C_3H_6$, $R_4=H$, and m and n are respectively 3.5 and 2.5 on average (mixture)) was used as a monofunctional aliphatic monomer other than butyl methacrylate (48 g).

The obtained resin particles were imaged under an SEM. The results show, as can be seen in the SEM image of FIG. 11, that the resin particles were non-spherical resin particles having such a shape that a portion of the quasi-sphere was missing to form a concave portion therein, and a convex portion with a quasi-spherical surface was formed in the concave portion. The SEM image of FIG. 11 also shows that roughness smaller than the convex and concave portions was formed (second concave portions smaller than the concave portion were formed) on the surface of a non-concave portion of the non-spherical resin particles (the surface of the quasi-spherical shell).

The average particle diameter of the obtained non-spherical resin particles was measured by the aforementioned method to be 2.5 μm. The CV value of the particle diameters of the obtained non-spherical resin particles was measured by the aforementioned method to be 10%, which indicates that the non-spherical resin particles were monodisperse particles.

Figure 11:
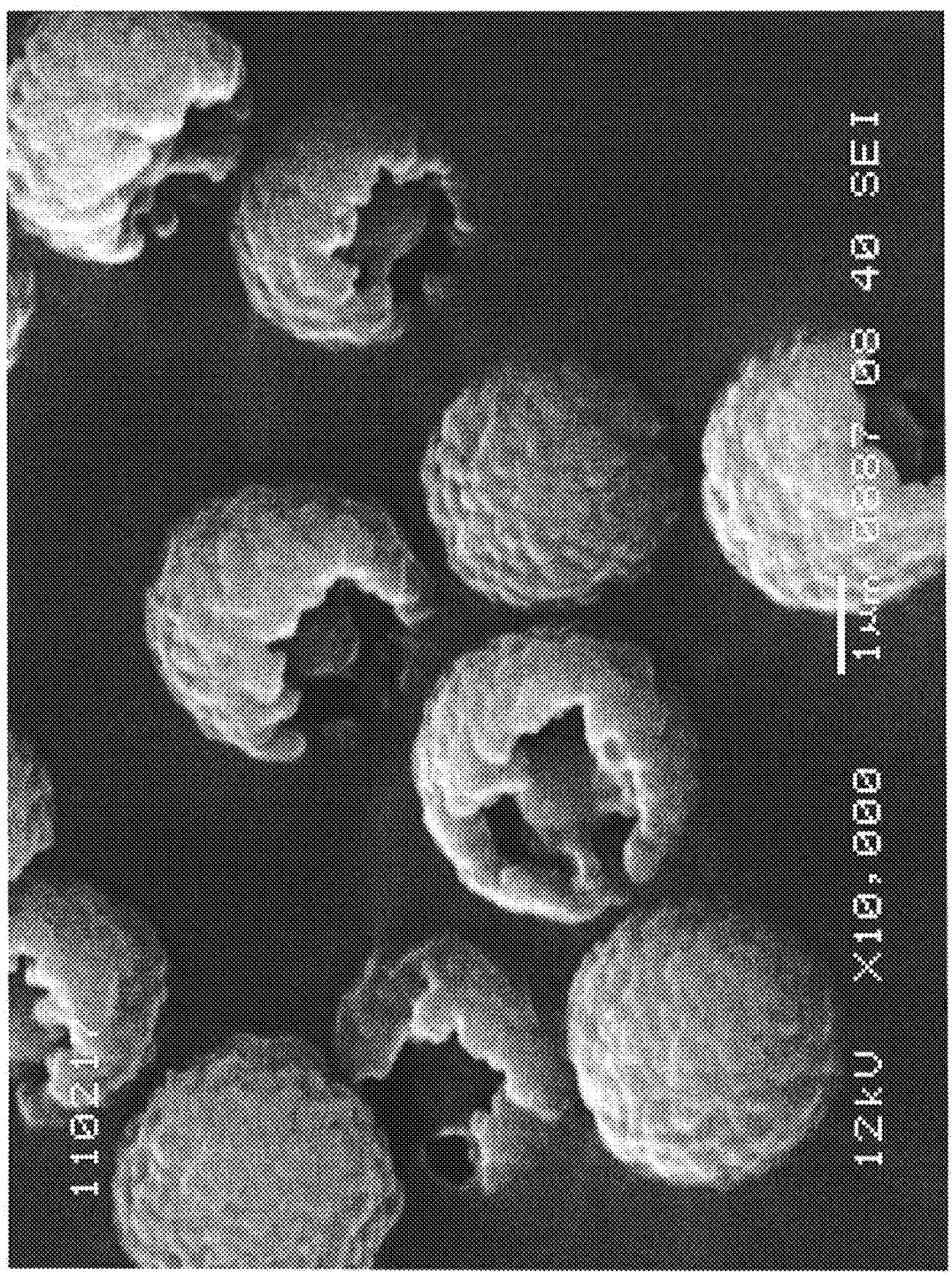
FIG. 11 is an image obtained from SEM imaging of the surface of a non-spherical resin particle obtained in example 5 of the present invention.

From the SEM image of FIG. 11, a maximum diameter "a" of the non-spherical resin particle was measured, and a diameter "b" of the convex portion b and a diameter "c" of the concave portion were estimated to calculate dimension ratios b/a and c/a. The estimated dimension ratios b/a and c/a were 0.42 and 0.32 respectively.

Example 6

Resin particles were prepared by the same manufacturing method as in example 1, except that 36.6 g of seed particles (5) obtained in seed particle preparation example 5 were used instead of seed particles (3) used in example 1.

The obtained resin particles were imaged under an SEM. The results show, as can be seen in the SEM image of FIG. 12, that the resin particles were non-spherical resin particles having such a shape that a portion of the quasi-sphere was missing to form a concave portion therein, and a convex portion with a quasi-spherical surface was formed in the concave portion. The SEM image of FIG. 12 also shows that roughness smaller than the convex and concave portions, but larger than the roughness on the surface of the non-spherical resin particles of examples 1 and 2 was formed (second concave portions smaller than the concave portion, but larger than the second concave portions on the surface of the shell of the non-spherical resin particles of examples 1 and 2 were formed) on the surface of a non-concave portion of the non-spherical resin particles (the surface of the quasi-spherical shell).

The average particle diameter of the obtained non-spherical resin particles was measured by the aforementioned method to be 2.5 μm. The CV value of the particle diameters of the obtained non-spherical resin particles was measured by the aforementioned method to be 10%, which indicates that the non-spherical resin particles were monodisperse particles.

Figure 12:
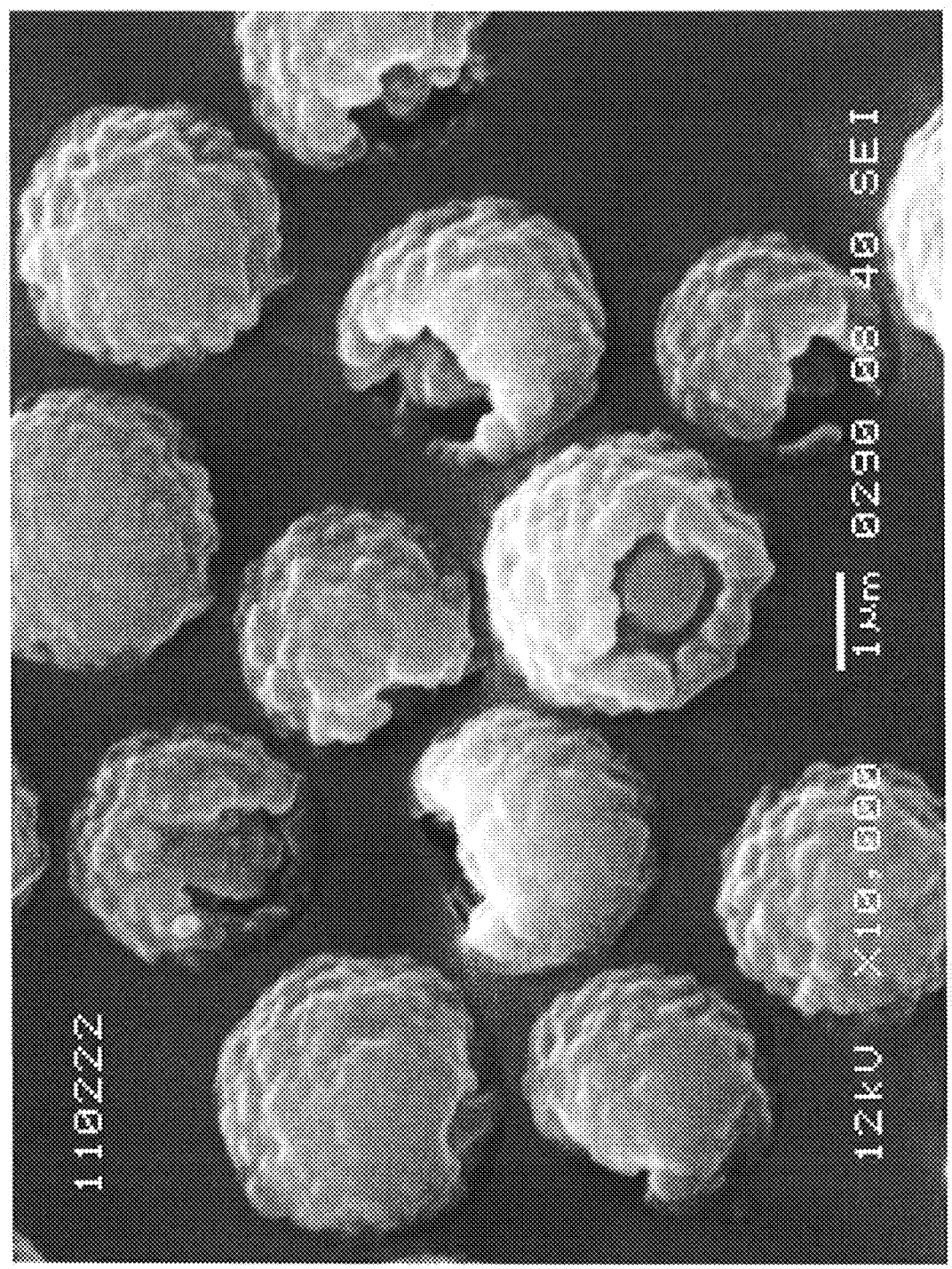
FIG. 12 is an image obtained from SEM imaging of the surface of a non-spherical resin particle obtained in example 7 of the present invention.

From the SEM image of FIG. 12, a maximum diameter "a" of the non-spherical resin particle was measured, and a diameter "b" of the convex portion b and a diameter "c" of the concave portion were estimated to calculate dimension ratios b/a and c/a. The estimated dimension ratios b/a and c/a were 0.44 and 0.42 respectively.

Table 1 collectively shows the dimension ratios b/a and c/a of the non-spherical resin particles of examples 1 to 6,

TABLE 1

|  | Example 1 | Example 2 | Example 3 | Example 4 | Example 5 | Example 6 |
|---|---|---|---|---|---|---|
| b/a | 0.36 | 0.30 | 0.51 | 0.43 | 0.42 | 0.44 |
| c/a | 0.50 | 0.35 | 0.50 | 0.26 | 0.32 | 0.42 |

Figure 13:
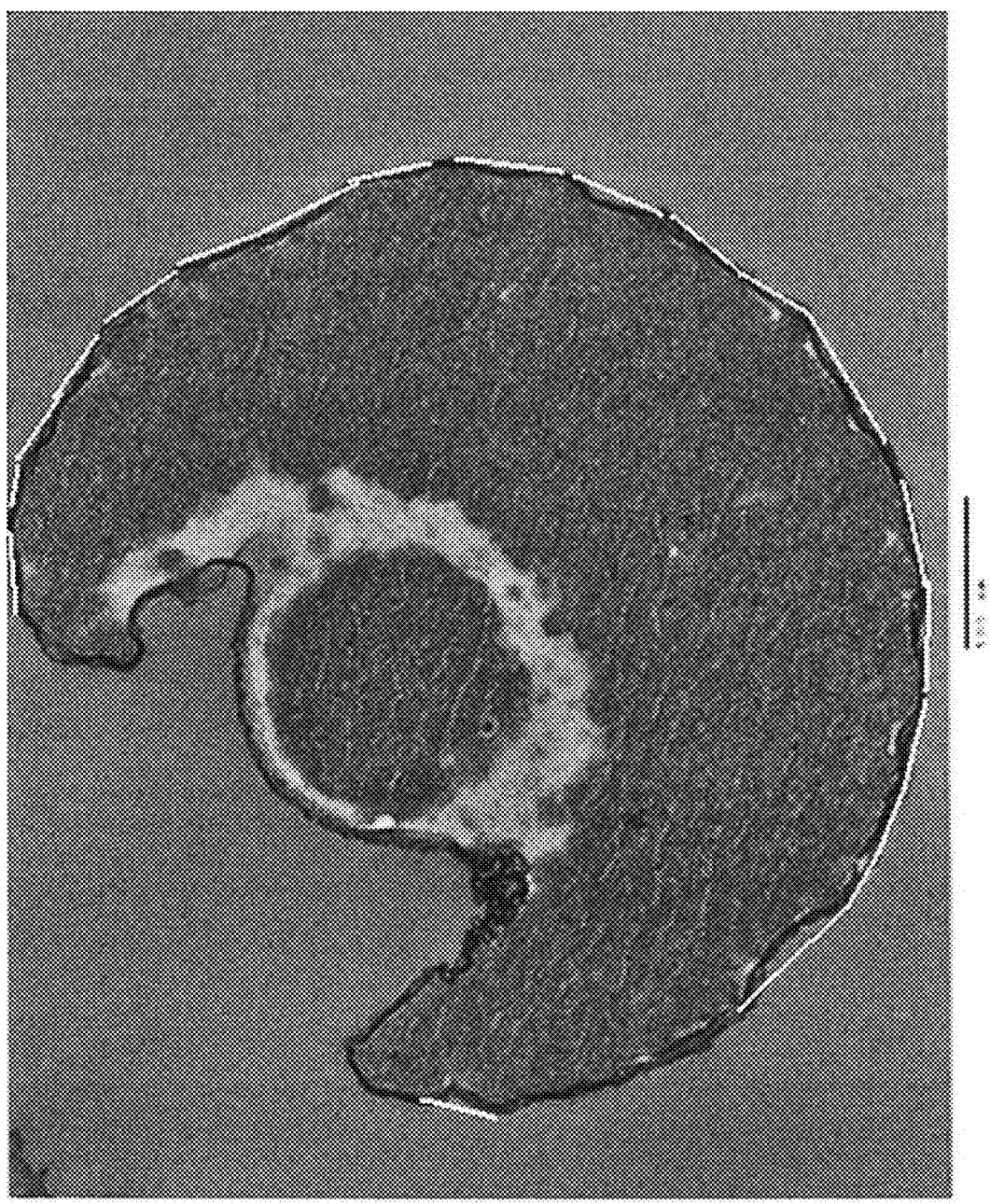
FIG. 13 is an illustration depicting a method of calculating a maximum depth of concave portions on the shell surface of a non-spherical resin particle of the present invention. The illustration shows white lines being drawn on the TEM image of FIG. 8 to indicate line segments for use in the calculation.

A maximum depth of second concave portions formed on the surface of the quasi-spherical shell of the non-spherical resin particles of examples 1 to 6 (surface of the non-concave portion of the non-spherical resin particles) was calculated as follows. In the TEM image (FIGS. 4, 6, 8, and 10) or the SEM image (FIGS. 11 and 12) of the non-spherical resin particles of examples 1 to 6, draw line segments connecting the top edges of the convex portions formed on the surface of the quasi-spherical shell. Find a point which is located deepest from the line segments on the surface of the quasi-spherical shell (a point, on the curved line representing the particle surface, which is located farthest from the line segments). From that point, draw a line normal to the line segment that is closest to the point. The length of the normal line is taken as a maximum depth of the second concave portions formed on the surface of the quasi-spherical shell. Table 2 shows the results of the calculation. FIG. 13 identifies the line segments drawn on the TEM image of FIG. 8 as white lines.

TABLE 2

|  | Example 1 | Example 2 | Example 3 | Example 4 | Example 5 | Example 6 |
|---|---|---|---|---|---|---|
| Maximum Depth of second concave portions on shell surface | 60 nm | 70 nm | 110 nm | 60 nm | 200 nm | 180 nm |

Comparative Example 1

Resin particles were prepared by the same manufacturing method as in example 1, except that 36.6 g of seed particles (2) obtained in seed particle preparation example 2 was used instead of seed particles (3) used in example 1.

Figure 14:
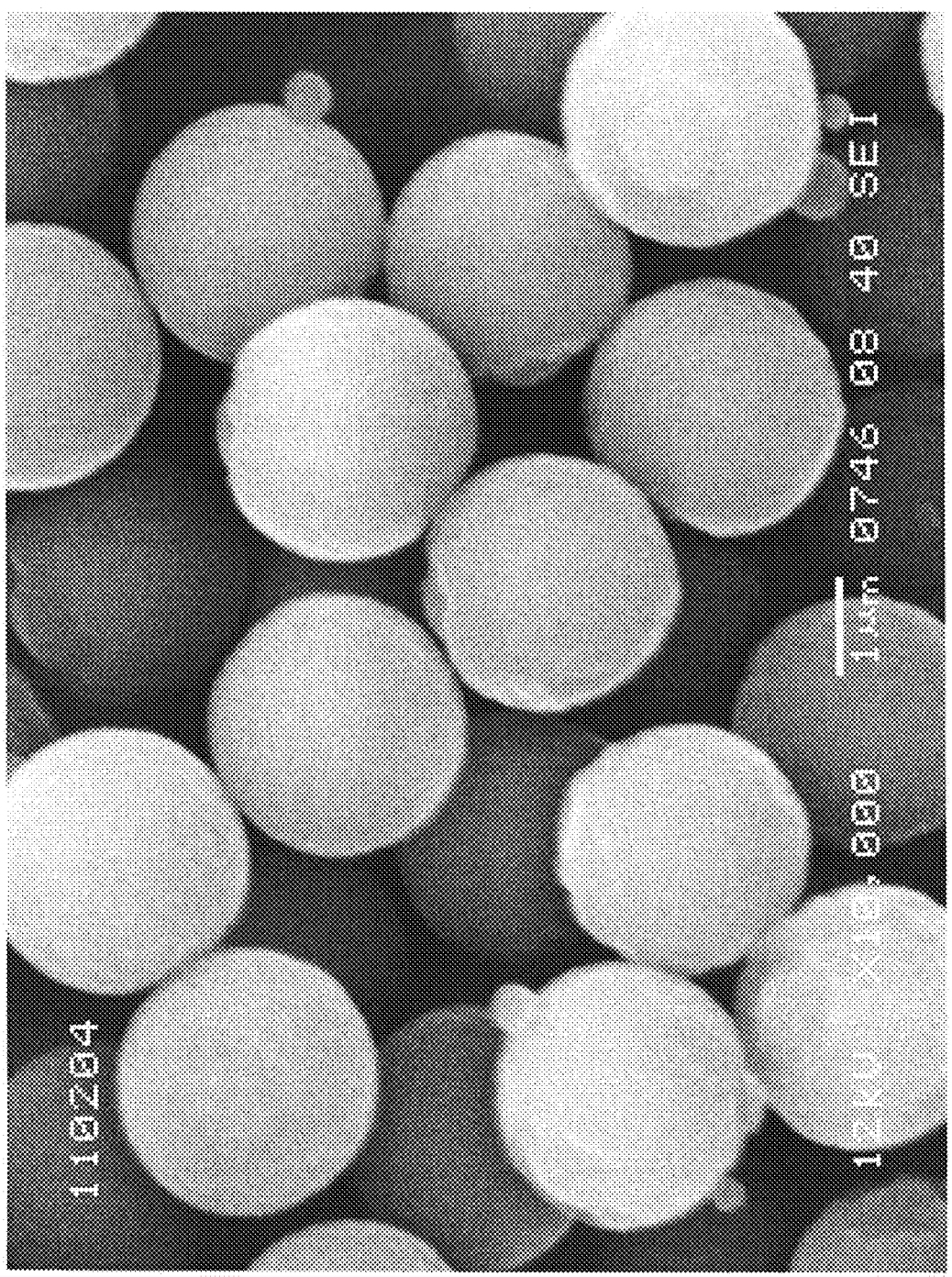
FIG. 14 is an image obtained from SEM imaging of the surface of a resin particle obtained in comparative example 1.

The obtained resin particles were imaged under an SEM. The results show, as can be seen from the SEM image of FIG. 14, that the resin particles were substantially spherical and did not have, on their surface, roughness which might correspond to those formed on the surface of the quasi-spherical shell of the non-spherical resin particles of examples 1 to 6.

The average particle diameter of the obtained resin particles was measured by the aforementioned method to be 2.5 μm. The CV value of the particle diameters of the obtained, resin particles was measured by the aforementioned method to be 11%, which indicates that the resin particles were monodisperse particles.

Comparative Example 2

Resin particles were prepared by the same manufacturing method as in example 1, except that 36.6 g of seed particles (2) obtained in seed particle preparation example 2 was used instead of seed particles (3) used in example 1 and also that isobutyl methacrylate (56 g), instead of butyl methacrylate (56 g), was used as a monofunctional aliphatic monomer.

Figure 15:
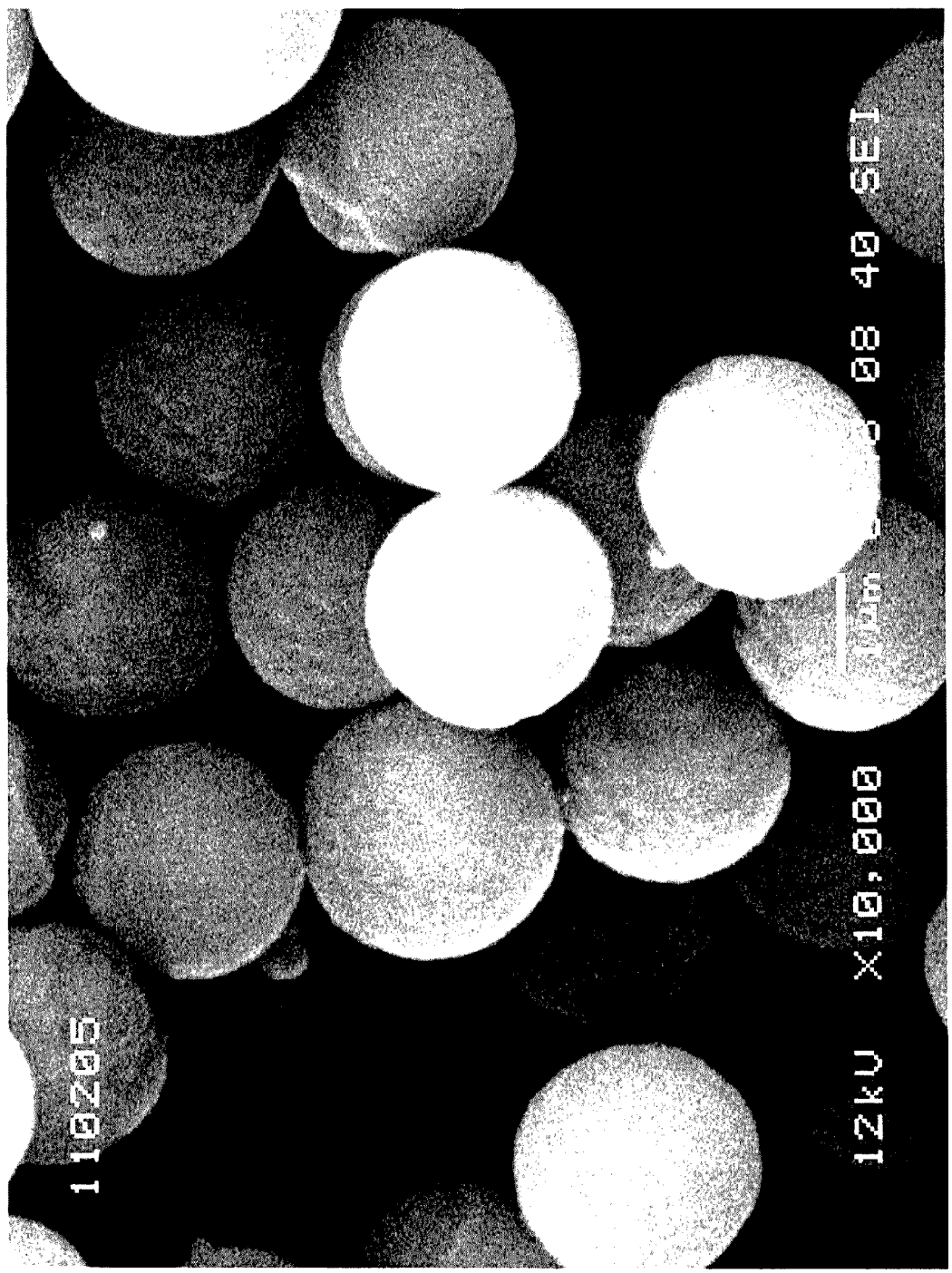
FIG. 15 is an image obtained from SEM imaging of the surface of a resin particle obtained in comparative example 2.

The obtained resin particles were imaged under an SEM. The results show, as can be seen from the SEM image of FIG. 15, that the resin particles were substantially spherical and did not have, on their surface, roughness which might correspond to those formed on the surface of the quasi-spherical shell of the non-spherical resin particles of examples 1 to 6.

The average particle diameter of the obtained resin particles was measured by the aforementioned method to be 2.5 μm. The CV (coefficient of variation) value of the particle diameters of the obtained resin particles was measured by the aforementioned method to be 12%, which indicates that the resin particles were monodisperse particles.

Comparative Example 3

Resin particles were prepared by the same manufacturing method as in example 1, except that 36.6 g of seed particles (4) obtained in seed particle preparation example 4 was used instead of seed particles (3) used in example 1.

Figure 16:
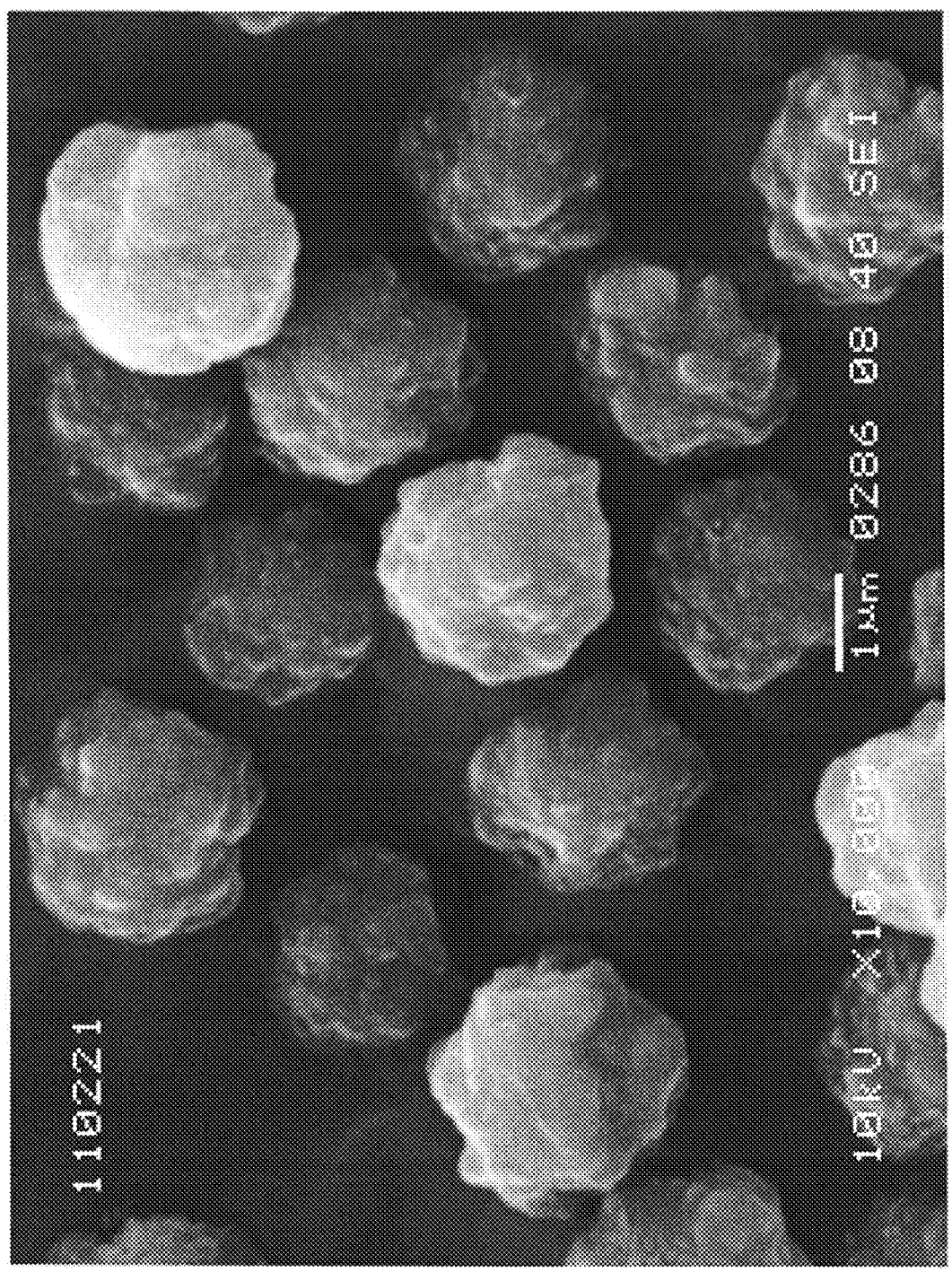
FIG. 16 is an image obtained from SEM imaging of the surface of a resin particle obtained in comparative example 3.

The obtained resin particles were imaged under an SEM. The results show, as can be seen in the SEM image of FIG. 16, that the resin particles were non-spherical, had creases all over the surface, and did not have, on their surface, roughness which might correspond to those formed on the surface of the quasi-spherical shell of the non-spherical resin particles of examples 1 to 6.

The average particle diameter of the obtained non-spherical resin particles was measured by the aforementioned method to be 2.5 μm. The CV value of the particle diameters of the obtained non-spherical resin particles was measured by the aforementioned method to be 10%, which indicates that the non-spherical resin particles were monodisperse particles.

Examples 1 to 6 in comparison with comparative examples 1 to 3 show that non-spherical resin particles having such a shape that a portion of the quasi-sphere is missing to form a concave portion therein, and a convex portion with a quasi-spherical surface is formed in the concave portion are obtained by polymerizing a branched alkyl methacrylate and a polyfunctional monomer in the presence of less than 1 part by weight of a chain transfer agent and a (meth)acrylate polymer to obtain resin particles, letting the resin particles to absorb a monomer mixture containing a monofunctional aliphatic monomer and a polyfunctional monomer, and then polymerizing the resin particles.

Comparative Example 4

Styrene (70 parts by weight), divinylbenzene (10 parts by weight), benzoyl peroxide (2.0 parts by weight), sodium dodecylbenzenesulfonate (0.5 parts by weight), sodium nitrite (0.1 parts by weight), and ion exchanged water (200 parts by weight) were stirred at 10,000 rpm for 3 minutes using a homogenizer mixer.

The mixture was transferred to a 1-liter, four-neck flask equipped with a thermometer and a nitrogen gas introduction tube. Seed particles (7) (76.2 parts by weight) were added, and the whole content was reacted at 75° C. for 3 hours and at 90° C. for another 3 hours to obtain a dispersion liquid. The polymerized reaction liquid was filtered to separate out resin particles from the reaction liquid. The separated resin particles were well washed in warm water and dried to obtain resin particles.

The obtained resin particles turned out to be semi-spherical (non-spherical) and have a swell at the center. The outer circumferential surface of the semi-sphere of the obtained resin particles is smooth and did not have a concave portion in the observation.

Measurement of Oil Absorption Value

The oil absorption values by the resin particles of examples 1, 3, and 4 and comparative example 2 were measured by a method based on the measuring method JIS K 5101-13-2. In the method actually implemented, JIS first grade linseed oil was used instead of boiled linseed oil, and the criteria for an end point were modified. The following will give more details about the measurement of the oil absorption value.

(A) Devices and Tools

Measurement plate: Flat and smooth glass plate larger than 300×400×5 mm.

Palette knife (spatula): Complete with a steel or stainless steel blade and a handle.

Analytical balance (weighing scale): Capable of measuring to the order of 10 mg.

Burette: As specified in JIS R 3505, with a capacity of 10 ml.

(B) Reagent

JIS First Grade Linseed Oil: manufactured by Wako Pure Chemical Co., Ltd.

(C) Measuring Method (1) Place 1 g of resin particles at the center of the measurement plate. Dispense JIS first grade linseed oil dropwise from the burette to the center of the resin particles gradually (4 or 5 drops at a time). For every dispensation, knead the entire resin particles and JIS first grade linseed oil well with a palette knife.

(2) Repeat the dispensation and kneading until the entire resin particles and JIS first grade linseed oil forms a hard putty lump. Then dispense the primary linseed oil a drop at a time, and knead for every dispensation until dispensing the last drop of the JIS first grade linseed oil abruptly softens the paste (kneaded product of the resin particles and the primary linseed oil) so that the paste starts flowing. This is taken as the end point.

(3) Criteria for flow

The paste is determined to be flowing if dispensing the last drop of the primary linseed oil abruptly softens the paste so that the paste slides on a vertically erected measurement plate. If the paste does not slide on the vertically erected measurement plate, another drop of the primary linseed oil is dispensed.

(4) Read out the decrease of liquid in the burette as the amount of the JIS first grade linseed oil consumed when the end point is reached.

(5) Carry out each round of measurement so that it is finished in 7 to 15 minutes. If any round of measurement lasts in excess of 15 minutes, do the measurement again. Only those numeric values which are obtained from rounds of measurement finishing in the specified time should be accepted.

(D) Calculation of Oil Absorption Value

The oil absorption value per 100 g of sample is calculated by the following equation.

$$O=(V/m)\times 100$$

where O is the oil absorption value (ml/100 g), m is the weight (g) of the resin particles, and V is the volume (ml) of JIS first grade linseed oil consumed.

Table 2 shows measurements of the oil absorption value for the resin particles of examples 1, 3, and 4, and comparative example 2. The oil absorption values in Table 2 are average values obtained from three rounds of measurement of the amount of oil which was absorbed by the resin particles.

Measurement of Specific Surface Area

The specific surface areas of the resin particles of examples 1, 3, and 4, and comparative example 2 were measured, using a micromeritics automatic surface area and porosimetry analyzer TriStar® 3000 manufactured by Shimadzu Corporation as a measuring instrument, by the BET (Brunauer-Emmett-Teller) method (nitrogen adsorption method) described in JIS R 1626. BET nitrogen adsorption isotherms were measured for the resin particles under observation using the micromeritics automatic surface area and porosimetry analyzer Tristar® 3000. The specific surface areas were calculated from the amounts of nitrogen adsorption by the BET multipoint method. The nitrogen adsorption isotherms were measured using nitrogen as an adsorbent by a constant volume method with the cross-sectional area of adsorbent being $0.162\ nm^2$.

Table 3 shows measurements of the specific surface areas of the resin particles for examples 1, 3, and 4, and comparative example 2. The specific surface areas in Table 3 are average values obtained from three rounds of measurement of the specific surface area of the resin particles for each example/comparative example.

TABLE 3

| | Oil Absorption Value (ml/100 g) | Specific Surface Area (m²/g) |
| --- | --- | --- |
| Examgle 1 | 110 | 2.87 |
| Example 3 | 170 | 3.25 |
| Example 4 | 180 | 3.30 |
| Comparative Example 2 | 92 | 1.98 |

The non-spherical resin particles of examples 1, 3, and 4 had a greater specific surface area, and absorbed more oil, than the spherical resin particles of comparative example 2. This is because the non-spherical resin particles of examples 1, 3, and 4 have a concave portion, hence a greater specific surface area than the spherical resin particles of comparative example 2, and an accordingly greater oil absorbing area. Therefore, using the non-spherical resin particles of examples 1, 3, and 4 in an external preparation (e.g., cosmetic liquid) or a coating material would give the resin particles a greater area to contact a medium (e.g., solvent), making the resin particles compatibly mixed with the medium (other components), or making the resin particles less likely to come off.

Example 7

Example of Blending of Non-Spherical Resin Particles into External Preparation

The non-spherical resin particles of example 1 (2 g), ion exchanged water (9 g), and ethanol (1 g) as a lower alcohol were mixed to prepare a body lotion as an example of the external preparation of the present invention.

Example 8

Example of Blending of Non-Spherical Resin Particles into External Preparation

A body lotion as an example of the external preparation of the present invention was prepared in the same manner as in example 7, except that the non-spherical resin particles of example 3 were used instead of the non-spherical resin particles of example 1.

Example 9

Example of Blending of Non-Spherical Resin Particles into External Preparation

A body lotion as an example of the external preparation of the present invention was prepared in the same manner as in example 7, except that the non-spherical resin particles of example 4 were used instead of the non-spherical resin particles of example 1.

Comparative Example 5

A comparative body lotion was prepared in the same manner as in example 7, except that the spherical resin particles of comparative example 2 were used instead of the non-spherical resin particles of example 1.

Evaluation of Moisture Retention (Moist Feeling)

The body lotions of examples 7 to 9 and comparative example 5 were applied to wrists of 10 subjects to conduct a sensory evaluation of moist skin feel by touching by a finger. Results of the sensory evaluation of moist feeling were calculated as an average score on the following evaluation scale of 1 to 5.

5 . . . Extremely moist
4 . . . Very moist
3 . . . Moderately moist
2 . . . Slightly moist
1 . . . Not moist Table 4 shows results of the sensory evaluation of moist skin feel for the body lotions of examples 7 to 9 and comparative example 5.

TABLE 4

|  | Example 7 | Example 8 | Example 9 | Comparative Example 5 |
|---|---|---|---|---|
| Moist Skin Feel | 4.2 | 4.4 | 4.5 | 3.8 |

The results show that the moisture retention of body lotion is related to the oil absorption value by the resin particles contained in the body lotion: the greater the specific surface area of the resin particles, the higher the moisture retention of the body lotion. The body lotions of examples 7 to 9 which contained the non-spherical resin particles of examples 1, 3, and 4 with a greater specific surface area exhibited higher moisture retention than the body lotion of comparative example 5 which contained the spherical resin particles of comparative example 2 with a smaller specific surface area.

Example 10

Example of Preparation of Light Diffusion Film

The non-spherical resin particles of example 1 (20 parts by weight) and an acrylic-based binder (20 parts by weight, trade name: Dianal® BR-116, manufactured by Mitsubishi Rayon Co., Ltd.) as a binder resin were mixed to obtain a mixture. A mixed solvent (180 parts by weight) obtained by mixing toluene and methyl ethyl ketone in a volume ratio of 1:1 was added to the obtained mixture. The whole mixture was stirred in a centrifugal stirrer for 3 minutes to obtain a solution. After being left to stand for 3 hours, the solution was stirred for another 3 minutes in the centrifugal stirrer to obtain a solution (light diffusing coating agent) as an example of the coating material of the present invention.

Thereafter, a 100-μm thick PET film as a transparent base material was coated with the obtained solution using a 75-μm coater. The obtained film was dried for 1 hour in a drier maintained at 70° C. to obtain a light diffusion film with a total thickness of (dry film thickness) of approximately 110 μm to 120 μm as an example of the light diffusion member of the present invention.

Example 11

Example of Preparation of Light Diffusion Film

A light diffusion film as an example of the light diffusion member of the present invention was obtained in the same manner as in example 10, except that the non-spherical resin particles of example 3 were used instead of the non-spherical resin particles of example 1.

Example 12

Example of Preparation of Light Diffusion Film

A light diffusion film as an example of the light diffusion member of the present invention was obtained in the same manner as in example 10, except that the non-spherical resin particles of example 4 were used instead of the non-spherical resin particles of example 1.

Comparative Example 6

A comparative light diffusion film was obtained in the same manner as in example 10, except that the spherical resin particles of comparative example 2 were used instead of non-spherical resin particles of example 1.

Comparative Example 7

A comparative light diffusion film was obtained in the same manner as in example 10, except that the non-spherical resin particles of comparative example 4 were used instead of the non-spherical resin particles of example 1.

Scratch Resistance Test of Light Diffusion Film (Unlikeliness of Resin Particles to Come Off)

The surface of the resin particle-containing layers (coats of light diffusing coating agents) of the light diffusion films of examples 10 to 12 and comparative examples 6 and 7 was polished 20 full cycles (back and forth 20 times) with cloth using a rubbing fastness tester. Development of scratches on the polished light diffusion film was visually observed.

The scratch resistance was rated "good" if three or fewer line scratches were observed on the polished light diffusion film, "fair" if four to nine line scratches were observed, and "poor" if 10 or more line scratches were observed. Table 5 shows results of the evaluation of the scratch resistance of the light diffusion films of examples 10 to 12 and comparative examples 6 and 7.

TABLE 5

|  | Example 10 | Example 11 | Example 12 | Comparative example 6 | Comparative example 7 |
|---|---|---|---|---|---|
| Scratch resistance | Good | Fair | Good | Poor | Fair |

The test shows that The non-spherical resin particles of examples 1, 3, and 4 with a greater specific surface area are compatibly mixed with the binder resin, less likely to come off from the light diffusion film, and less prone to scratches developing on the light diffusion film surface (better scratch resistance of the light diffusion film) than the spherical resin particles of comparative example 2 with a smaller specific surface area.

Evaluation of Light Diffusion of Light Diffusion Film

Light diffusion by the light diffusion films of examples 10 to 12 and comparative examples 6 and 7 was evaluated by haze measurement which was carried out by a method based on JIS K 7136 using a haze meter ("NDH2000," manufactured by Nippon Denshoku Industries Co., Ltd) as a measuring instrument. Table 6 shows results of the evaluation of light diffusion by the light diffusion films of examples 10 to 12 and comparative example 6. The haze levels in Table 6 are an average over three measurements of the haze of each light diffusion film.

TABLE 6

|  | Example 10 | Example 11 | Example 12 | Comparative example 6 | Comparative example 7 |
|---|---|---|---|---|---|
| Haze (%) | 87.5 | 89.2 | 90.2 | 79.5 | 91.3 |

A comparison of the light diffusion films of examples 10 to 12 containing the non-spherical resin particles of examples 1, 3, and 4 and the light diffusion film of comparative example 6 containing the spherical resin particles of comparative example 2 show that the light diffusion films of examples 10 to 12 had a higher haze level and diffused more light than the light diffusion film of comparative example 6. These differences were presumably due to the difference in shape between the non-spherical resin particles of examples 1, 3, and 4 and the spherical resin particles of comparative example 2.

Measurement of Total Light Transmittance of Light Diffusion Film

The total light transmittance of the light diffusion films of examples 10 to 12 and comparative examples 6 and 7 was measured according to JIS K 7136 using a haze meter ("NDH2000," manufactured by Nippon Denshoku Industries Co., Ltd). Table 7 shows results of the measurement.

TABLE 7

|  | Example 10 | Example 11 | Example 12 | Comparative example 6 | Comparative example 7 |
|---|---|---|---|---|---|
| Total light transmittance (%) | 86.8 | 85.3 | 85.9 | 82.0 | 81.2 |

A comparison of the light diffusion films of examples 10 to 12 containing the non-spherical resin particles of examples 1, 3, and 4, the light diffusion film of comparative example 6 containing the spherical resin particles of comparative example 2, and the light diffusion film of comparative example 7 containing the non-spherical resin particles of comparative example 4 shows that the light diffusion films of examples 10 to 12 had a higher total light transmittance than the light diffusion films of comparative examples 6 and 7.

The light diffusion films of examples 10 to 12 had a higher total light transmittance than the light diffusion film of comparative example 7 presumably because the non-spherical resin particles of examples 1, 3, and 4, having both the shell and the inner core being made of an acrylic-based resin (a polymer of a vinyl-based monomer containing 50 wt % or more alkyl (meth)acrylate), had a relatively small difference in refractive index between the shell and the inner core, whereas the non-spherical resin particles of comparative example 4, having the inner core being made of a silicone resin and the shell being made of an acrylic-based resin and a styrene-based resin (styrene polymer), had a relatively large difference in refractive index between the shell and the inner core. The difference in refractive index between the shell and the inner core of the non-spherical resin particles of examples 1 to 6 is less than or equal to 0.05 and is probably in the range of 0.001 to 0.03. In contrast, the refractive index of a silicone resin is approximately 1.38 to 1.43, the refractive index of polymethyl methacrylate, which is a typical acrylic-based resin, is 1.49, and the refractive index of polystyrene, which is a typical styrene-based resin, is 1.59. Therefore, the difference in refractive index between the shell and the inner core of the non-spherical resin particles of comparative example 4 is probably greater than 0.05.

INDUSTRIAL APPLICABILITY

The present invention may be used in the manufacture of non-spherical resin particles which are used as a light diffusing agent constituting light diffusers, such as light diffusion films, light diffusion plates, and LED light covers; a light diffusing agent constituting light diffusing coating agents, such as coating materials, paper coating agents, and light diffusion film coating agents; a light diffusing agent constituting anti-glare films; and an additive for cosmetics (slip enhancement agent).

REFERENCE SIGNS LIST

1 Shell
2 Inner Core (Convex Portion)
2a Convex Surface (Quasi-spherical Surface)
3 Cavity (Concave Portion)

The invention claimed is:

1. Non-spherical resin particles, wherein each of the non-spherical resin particles comprises a contiguous surface, wherein the contiguous surface comprises:
   a first concave portion;
   a convex portion formed in the first concave portion; and
   a spherical portion;
   wherein the convex portion has a quasi-spherical surface;
   and wherein the contiguous surface forms a cavity between the spherical portion and the convex portion;
   wherein each of the non-spherical resin particles has a diameter represented by "a";
   the convex portion of said each of the non-spherical resin particles has a diameter represented by "b";
   the first concave portion of said each of the non-spherical resin particles has a diameter represented by "c";
   and wherein the ratio of b/a is in the range of 0.25 to 0.70 and the ratio of c/a is greater than 0.20.

2. The non-spherical resin particles as set forth in claim 1, wherein the surfaces of the spherical portions of said non-spherical resin particles have one or more second concave portions smaller than the first concave portions of the non-spherical resin particles.

3. The non-spherical resin particles as set forth in claim 1, wherein:
   each of the non-spherical resin particles has a second concave portion smaller than the first concave portion of said each of the non-spherical resin particles on a surface of a spherical portion of said each of the non-spherical resin particles; and
   the second concave portion has a maximum depth of greater than or equal to 50 nm and less than or equal to 500 nm.

4. The non-spherical resin particles as set forth in claim 1, wherein said particles have diameters with a coefficient of variation of less than or equal to 15%.

5. A method of manufacturing non-spherical resin particles of claim 1, comprising:
   the first step of polymerizing 100 parts by weight of a first monomer mixture containing 77 to 99.99 parts by weight of a branched alkyl methacrylate, 0.01 to 3 parts by weight of a polyfunctional monomer, and 0 to 20 parts by weight of a monofunctional (meth)acrylate which is not a branched alkyl methacrylate, in the presence of 0.1 to 0.9 parts by weight of a chain transfer agent and 0 to 100 parts by weight of a (meth)acrylate polymer, to obtain resin particles; and
   the second step of letting the obtained resin particles to absorb a second monomer mixture containing a monofunctional aliphatic monomer and a polyfunctional monomer, and thereafter polymerizing the resin particles,
   wherein in the second step, the polyfunctional monomer is used in an amount of from 5 to 50 wt % to the amount of the monofunctional aliphatic monomer being used.

6. The method as set forth in claim 5, wherein in the second step, 5 to 50 parts by weight of the resin particles absorb 100 parts by weight of the second monomer mixture.

7. An external preparation, comprising the non-spherical resin particles as set forth in claim 1.

8. A coating material, comprising the non-spherical resin particles as set forth in claim 1.

9. A light diffusion member, comprising the non-spherical resin particles as set forth in claim 1.

\* \* \* \* \*